United States Patent
Schmitthenner et al.

(10) Patent No.: US 10,927,132 B2
(45) Date of Patent: Feb. 23, 2021

(54) TRANSMETALATION METHODS FOR THE SYNTHESIS OF PET AND SPECT IMAGING AGENTS

(71) Applicants: Hans F. Schmitthenner, Rush, NY (US); Anne M. Sweeney-Jones, Rochester, NY (US); Scott Williams, Livonia, NY (US)

(72) Inventors: Hans F. Schmitthenner, Rush, NY (US); Anne M. Sweeney-Jones, Rochester, NY (US); Scott Williams, Livonia, NY (US)

(73) Assignee: Rochester Institute of Technology, Rochester, NY (US)

( * ) Notice: Subject to any disclaimer, the term of this patent is extended or adjusted under 35 U.S.C. 154(b) by 0 days.

(21) Appl. No.: 15/055,203

(22) Filed: Feb. 26, 2016

(65) Prior Publication Data

US 2016/0251378 A1  Sep. 1, 2016

Related U.S. Application Data

(60) Provisional application No. 62/126,035, filed on Feb. 27, 2015.

(51) Int. Cl.

| | |
|---|---|
| *A61K 51/00* | (2006.01) |
| *A61M 36/14* | (2006.01) |
| *C07F 5/00* | (2006.01) |
| *C07F 1/00* | (2006.01) |
| *A61K 51/08* | (2006.01) |
| *B01D 15/38* | (2006.01) |
| *B01D 15/42* | (2006.01) |
| *C07F 1/08* | (2006.01) |
| *B01D 15/32* | (2006.01) |

(52) U.S. Cl.
CPC .............. *C07F 5/00* (2013.01); *A61K 51/082* (2013.01); *A61K 51/088* (2013.01); *B01D 15/3857* (2013.01); *B01D 15/426* (2013.01); *C07F 1/005* (2013.01); *C07F 1/08* (2013.01); *C07F 5/003* (2013.01); *B01D 15/325* (2013.01)

(58) Field of Classification Search
CPC .......... C07F 5/00; C07F 1/08; B01D 15/3857; B01D 15/426
USPC ....................................................... 424/1.81
See application file for complete search history.

(56) References Cited

U.S. PATENT DOCUMENTS

| | | | |
|---|---|---|---|
| 2004/0022733 A1 | 2/2004 | Uzgiris | |
| 2008/0279771 A1* | 11/2008 | Kindberg | A61K 51/088 424/1.69 |
| 2009/0155167 A1* | 6/2009 | Powell | A61K 51/025 424/1.61 |
| 2013/0149244 A1 | 6/2013 | Purohit et al. | |
| 2014/0004041 A1 | 1/2014 | Ivson et al. | |
| 2014/0186850 A1 | 7/2014 | Berniac et al. | |
| 2015/0038672 A1 | 2/2015 | Schmitthenner et al. | |

OTHER PUBLICATIONS

Choi et al. Bull. Chem. Soc. Jpn. 67, 267-270 (1994).*

J.P. Holland, F.I. Aigbirhio, H.M. Betts,. P. D. Bonnitcha, P.Burke, M. Christlieb, G.C. Churchill, A.R. Cowley, J.R. Dilworth, P.S. Donnelly, J. C. Green, J.M. Peach, S.R. Vasudevan, J.E. Warren, "Functionalized Bis (thiosemicarbazonato) Complexes of Zinc and Copper: Synthetic Platforms Toward Site-Specific Radiopharmaceuticals", Inorg. Chem., 2007, 46 (2), pp. 465-485.

H.M. Betts, P.J. Barnard, S.R. Bayly, J.R. Dilworth, A.D. Gee, J.P. Holland, "Controlled axial coordination: solid-phase synthesis and purification of metallo-radiopharmaceuticals", Angew Chem Int Ed Engl. 2008;47(44):8416-9.

R. Uppal, C. Catana, I. Ay, et al, "Bimodal Thrombus Imaging:Simultaneous PET/MR Imaging with a Fibrin-targeted Dual PET/MR Probe—Feasibility Study in Rat Model," Radiology, vol. 258, No. 3, pp. 812-820, 2011.

M. Suchy, R. Bartha, and R. Hudson, ""Click" chemistry toward bis(DOTA-derived) heterometallic complexes: potential bimodal MRI/PET(SPECT) molecular imaging probes," RSC Adv., vol. 3, pp. 32493259, 2013.

C. Gros, A. Eggenspiller, A. Nonat, et al, "New potential bimodal imaging contrast agents based on DOTA-like and porphyrin macrocycles," Med. Chem. Comm., vol. 2, pp. 119-125, 2011.

M. Shokeen, C. Anderson, "Molecular Imaging of Cancer with Copper-64 Radiopharmaceuticals and Positron Emission Tomography (PET)," Accounts of Chem. Research, vol. 42, No. 7, pp. 832-841, 2009.

T. Wadas, E. Wong, G. Weisman, C. Anderson, "Coordinating Radiometals of Copper, Gallium, Indium, Yttrium and Zirconium for PET and SPECT Imaging of Disease," Chem. Rev., vol. 110, No. 5, pp. 2858-2902, 2010.

W. Cacheris, S. Nickle, A. Sherry, Inorg. Chem. Thermodynamic study of lanthanide complexes of 1,4,7-triazacyclononane-N,N',N"-triacetic acid and 1,4,7,10-tetraazacyclododecane-N,N',N",N"-tetraacetic acid, vol. 26, pp. 958-960, 1987.

(Continued)

*Primary Examiner* — Michael G. Hartley
*Assistant Examiner* — Sean R Donohue
(74) *Attorney, Agent, or Firm* — Bond, Schoeneck & King, PLLC; Joseph Noto

(57) ABSTRACT

A process for the preparation of a radionuclide imaging agent includes providing an imaging agent including a chelated place-holder metal; loading the imaging agent onto an acid stable stationary phase; replacing the chelated place-holder metal of the imaging agent loaded on the stationary phase with a replacement radioactive metal under mild reaction conditions; and eluting the imaging agent including the chelated replacement radioactive metal from the stationary phase to provide a radionuclide imaging agent suitable for positron emission tomography (PET) or single-photon emission computed tomography (SPECT). The imaging agent can include a targeting agent that is directly conjugated to the imaging agent or by means of a linker. The process may also apply to other metals that are non-radioactive but used as diluent metals or other metals that are strongly bound to DOTA.

13 Claims, 5 Drawing Sheets

(56) References Cited

OTHER PUBLICATIONS

A. Pasha, G. Tircso, E.T. Benyo, E. Bracher, and A.D. Sherry, "Synthesis and characterization of DOTA-(amide)4 derivatives: equilibrium and kinetic behavior of their lanthanide(III) complexes," Eur. J. Inorg. Chem., pp. 4340-4349, 2007.

N. Viola-Villegas, R. Doyle, "The coordination chemistry of 1,4,7,10-tetraazacyclododecane-N,N , N,N-tetraacetic acid (H4DOTA): Structural overview and analyses on structure-stability relationships", Coord. Chem. Rev. vol. 253, pp. 1906-1925, 2009.

International Search Report and Written Opinion in corresponding international application (PCT/US2016/019892) dated May 3, 2016.

EPO Form 1507 and Search Report, EP Application No. 16 756 488.9, pp. 1-8, dated Dec. 13, 2018.

\* cited by examiner

TRANSMETALATION METHODS FOR THE SYNTHESIS OF PET AND SPECT IMAGING AGENTS

CROSS REFERENCE

This application claims the benefit of the filing date of U.S. Provisional Patent Application Ser. No. 62/126,035, filed Feb. 27, 2015, which is hereby incorporated by reference in its entirety.

FIELD

The disclosure relates to a method for the synthesis of PET and SPECT imaging agents, and in particular to the synthesis of PET and SPECT targeted imaging agents.

BACKGROUND

Molecular imaging is a rapidly growing field that allows for early detection, accurate diagnosis, drug development and guided treatment of diseases including cancer, heart disease, disorders of the brain and many others. Radionuclide imaging, including positron emission tomography (PET) and single-photon emission computed tomography (SPECT), is among the most successful molecular imaging techniques with remarkable advances in instrumentation including 3-D imaging. PET and SPECT are carried out through the use of a positron-emitting radionuclide that is incorporated in a pharmacologically significant molecule that can target a tissue or organ of interest.

Radionuclides may be considered to be in two main groups, metals and non-metals. The use of metal positron-emitting radionuclides, such as $^{64}$Cu, $^{68}$Ga, $^{86}$Y, $^{89}$Zr, $^{99}$Tc, and $^{111}$In embedded in chelating complexes is gaining interest since they have longer half-lives compared to the non-metal PET isotopes $^{18}$F, $^{15}$O, $^{13}$N, and $^{11}$C. These transition metal radionuclides have become widely available and the longer half-lives accommodate the time frame required to study a wide variety of biological processes.

Current synthetic methods to create imaging agents for PET which contain metals are of two types. In the first method, the targeting agent of interest is first bonded to a chelating group, such as DOTA, and then a radioactive metal is inserted in the last steps of the synthesis. As DOTA contains three acidic and four amine moieties, the conjugation is often complicated by byproducts, multiple conjugates which are difficult to control and the purification of conjugates prior to introduction of the radionuclide metal may be difficult.

In a second widely used synthetic approach, a protected version of DOTA, such as tri-t-butyl DOTA, is utilized as a precursor to facilitate introduction of the DOTA to the targeting agent of interest. However, this requires deprotection under harsh acidic conditions (such as pure trifluoroacetic acid) followed by chelation of the radioactive metal in the final steps of the synthesis. Many targeting agents or biological labels are not robust enough to withstand the harsh deprotection steps needed to remove the t-butyl protecting groups from the DOTA. These limitations severely limit the options for targeting groups to the use of stable peptides and drug-like molecules or inhibitors and preclude the use of many other proteins, antibodies, aptamers and many more sensitive peptides.

The available lifetime of the radionuclide is a further limiting factor in the synthesis and use of PET and SPECT agents. Extended synthetic steps or purification steps after introduction of the radionuclide may consume the valuable time available during the radioactive decay. For these reasons the reported synthesis of targeted and non-targeted molecular imaging agents for PET and SPECT introduce the DOTA groups either directly or after deprotection, followed by introduction of the radioactive metal in the final step.

U.S. Patent Application Publication No. US 2015/0038672, which is hereby incorporated by reference in its entirety, discloses the use of a chelated metal such as cerium (Ce) for the dual purpose as a protecting group and as a precursor to a PET or SPECT agent. The method includes a procedure for synthesizing imaging agents for PET and SPECT by introduction of a "place-holder metal" such as cerium (Ce) which could be removed and replaced by a one-step or two-step solution transmetalation in the final steps of the modular synthesis of targeted molecular imaging agents. In that application copper (Cu) was used as a model for a radionuclide.

In that application a series of model studies was reported utilizing an Fmoc protected Lysine containing a DOTA group on the side chain to which a metal was chelated. In that application the metal gadolinium (Gd) was utilized and carried on through a number of synthetic steps including deprotection steps, coupling steps to additional amino acids, addition of a linker, and conjugation of a cancer targeting peptide. It was shown that Ce could likewise be chelated and further shown that Ce could be transmetalated to Cu by the use of treatment in solution with mild acid (0.1 or 0.2 M trifluoroacetic acid, TFA) followed by Cu(NO)$_3$, either as a one step or two step process in solution.

In the prior application we have shown that the transmetalation can be accomplished in solution via a one-step trans-metalation or in a two-step process where the imaging agent containing the chelate and place-holder metal is de-metalized first to yield the unprotected DOTA itself, followed by re-metalation with a radioactive metal in the same vessel.

The method described in our prior application necessitated reaction times longer than one day for complete transmetalation under mild acidic conditions. Stronger acid led to faster transmetalation but these conditions are not conducive for acid sensitive targeting groups, such as certain peptides and antibodies. In mild acid the process required more than one and less than seven days to complete conversion, in acid strengths ranging from 0.1 to 0.5 molar TFA using either a one or two step solution process. Stronger acid may lead to shorter reaction times but is not a desirable medium for molecular imaging agents, notably those composed of sensitive targeting groups.

In that application the non-radioactive copper, Cu$^{2+}$ was utilized as a model for radioactive $^{64}$Cu. Other metals used in PET and SPECT including $^{64}$Cu, $^{68}$Ga, $^{86}$Y, $^{89}$Zr, $^{99}$Tc, and $^{111}$In are also strongly bound in DOTA and may be utilized in the same manner as Cu complexes.

SUMMARY

In accordance with one aspect of the present disclosure, there is provided a process for the preparation of a radionuclide imaging agent, including: providing an imaging agent including a chelated place-holder metal; loading the imaging agent onto an acid stable stationary phase; replacing the chelated place-holder metal of the imaging agent loaded on the stationary phase with a replacement radioactive metal under mild reaction conditions; and eluting the imaging agent including the chelated replacement radioactive metal from the stationary phase to provide a radionuclide imaging agent suitable for positron emission tomography or single-photon emission computed tomography.

In accordance with another aspect of the present disclosure, there is provided a process for the preparation of a targeted radionuclide imaging agent, including: providing a targeted imaging agent including a chelated place-holder metal; loading the imaging agent onto an acid stable stationary phase; replacing the chelated place-holder metal of the imaging agent loaded on the stationary phase with a replacement radioactive metal under mild reaction conditions; and eluting the imaging agent including the chelated replacement radioactive metal from the stationary phase to provide a targeted radionuclide imaging agent suitable for positron emission tomography or single-photon emission computed tomography.

In accordance with another aspect of the present disclosure, there is provided a kit including: an HPLC column including an acid stable stationary phase; an imaging agent including a chelated place-holder metal; and at least one of a dilute aqueous solution of strong acid (pKa<about 2) in a concentration of about 1.0 M or less and a solution of a weak organic acid (pKa>about 2 and <about 5) in a concentration of about 5.0 M or less.

These and other aspects of the present disclosure will become apparent upon a review of the following detailed description and the claims appended thereto.

DETAILED DESCRIPTION

Disclosed is a process for the preparation of an imaging agent, including providing imaging agents having a chelated place-holder metal, for example, $La^{3+}$ or chelated $Ce^{3+}$ or chelated $Ba^{2+}$, loading the imaging agents onto an acid stable stationary phase; replacing in at least a portion of the imaging agents loaded on the stationary phase the place-holder metal with a replacement radioactive metal under mild reaction conditions; and eluting the imaging agents having the chelated replacement radioactive metal from the stationary phase to provide a radionuclide imaging agent suitable for positron emission tomography or single-photon emission computed tomography. Optionally, the imaging agent is attached to a targeting agent to provide a targeted imaging agent.

The use of lanthanum (La), barium (Ba), and strontium (Sr) which neighbor Ce on the Periodic Table of Elements are also suitable for use in the present process. For example La is more easily displaced with more rapid kinetics of displacement and transmetalation. Place-holder metals suitable for use in the present disclosure include those chosen from the Group 1 and 2 metals from Rows 4, 5 and 6 on the Periodic Table of Elements (e.g., $K^+$, $Ca^{2+}$ and those alkali metals and rare earth metals below), as well as Group 3, 4, 5 and 6 of Row 6, which are known as the Lanthanide metals.

Figure 2:
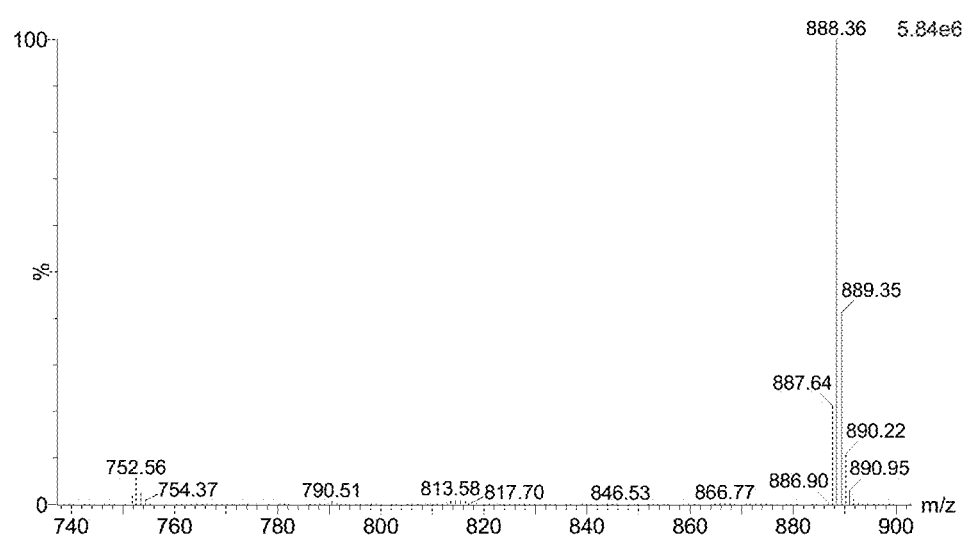
FIG. 2 is a mass spectra assay according to Comparative Example A.

As a result of reaction kinetics, displacement of place-holder metals, such as Ce, La, Ba, and Sr, is feasible under conditions in which europium (Eu) and gadolinium (Gd) (Group 9 and 10 in Row 6) are stable as shown in FIG. 2. One outcome of this is that a Gd chelate can remain intact during the transmetalation process for use as an MRI agent in the same molecule as a place-holder metal from those listed above, which can be transmetalated with a radioactive metal in order to make a dual imaging agent for MRI-PET or MRI-SPECT.

Alternative chelating groups to DOTA, including for example, DTPA, NOTA, TETA, NOTA, TACN, CB-TE2A, Cyclen, DO2A, DO3A, DOT, DOTAM, CB-Cyclam are expected to mirror DOTA in terms of transmetalation reactions and are suitable for use in the present disclosure.

An embodiment of the process includes transmetalation of targeted and non-targeted imaging agents containing place-holder metals. Targeting agents which are stable to treatment under mild reaction conditions during the transmetalation process are suitable for use in the present disclosure and include representative peptides cholesystokinin derivative CCK-4 amide and cyclic integrin peptide c(RGDyK), and include a wide variety of peptides, proteins, antibodies, nanobodies, aptamers and other targeting agents, such as active site inhibitors.

An embodiment includes a process for carrying out transmetalation on a stationary phase by loading a solution of the precursor targeted or non-targeted imaging agent onto the solid support upon which transmetalation will be performed. A suitable solid support includes a chromatography column containing a reverse phase (C18) solid support, ion exchange, polymer or affinity chromatography beads, particles or other chromatography media or solid supports used in peptide synthesis.

An embodiment of a process for transmetalation of a place-holder metal by replacing, for example the chelated $La^{3+}$ or chelated $Ce^{3+}$ or chelated $Ba^{2+}$ of the imaging agent loaded on the stationary phase with a chelated replacement radioactive metal under mild reaction conditions by the use of a HPLC pump or equivalent includes providing a flow through the column or packing material of a solution containing a mild acid and a solution containing a radioactive metal or diluted solution of radioactive and non-radioactive metal to markedly increase the rate of transmetalation. The solutions may be applied together in a one-step process or separately in a two-step process including adding the mild acid for a requisite time and then the solution containing radioactive metal for a comparatively much shorter time.

An embodiment of a process in accordance with the present disclosure includes a one-step transmetalation which can be completed in a period of time of about eight hours or less using a flow through the stationary phase under the mild reaction conditions of either: (a) a dilute aqueous solution of strong acid (pKa<about 2), such as trifluoroacetic acid, oxalic acid, hydrochloric or phosphoric acid in a concentration of about 1.0 M or less; or (b) a weak acid (pKa>about 2 and <about 5), such as organic acids of formic acid, citric acid, chloracetic acid, maleic acid, citric acid, acetic acid or glycolic acid in a concentration of about 5.0 M or less. The mild acidic solution is mixed before introduction to the pump, or by use of a mixing valve or two-pump system for delivery of a second solvent to the column containing the radioactive metal of choice dissolved in an aqueous concentration matched stoichiometrically to the concentration of the substrate to be chelated, or a solution containing a radioactive metal at the point of introduction to the column. Suitable solutions containing a radioactive metal include a solution containing a molarity of from about 0.01 M to about 5.0 M radioactive metal. In a preferred embodiment the mild acidic solution is preferably from about 0.05 M to about 1.0 M trifluoroacetic acid, or other organic acids including formic acid, citric acid, chloracetic acid, oxalic acid, maleic acid, citric acid, or hydroxy acetic acid.

An embodiment of a process in accordance with the present disclosure includes a two-step transmetalation under mild reaction conditions including flowing a first solution of strong acid or weak acid at the concentrations described in the one-step process above for a period of time of less than about 24 hours, followed by flowing a solution containing a stoichiometric or excess or reduced ratio of radioactive metal of choice dissolved in an aqueous concentration as described for the one-step process above with the second step taking a period of time of less than about 8 hours. Preferably, the two-step transmetalation is complete in a total period of time of less than about 24 hours.

An embodiment includes a process for eluting the imaging agent having the chelated replacement radioactive metal from the stationary phase to provide a radionuclide imaging agent suitable for positron emission tomography or single-photon emission computed tomography by changing the composition of the solution by a step change or gradient change in solvent, such as addition of an organic solvent such as methanol or acetonitrile to the aqueous solvent, or by replacing the aqueous solvent partially or completely by organic solvent in an isocratic or gradient elution, so that the final product is eluted into a fraction collector or other method of collection of product in under an about 8 hour time frame after replacement by the radioactive metal. Alternative methods for elution in the case of ion exchange or affinity stationary phases include changing the salt concentration of the solvent or the pH or the solvent.

An embodiment includes a process for transmetalation of a targeted imaging agent for PET or SPECT in which suitable targeting agents include those chosen from peptides, proteins, antibodies, nanobodies, aptamers and other targeting agents, such as active site inhibitors. The targeting agent may be directly attached to the imaging agent portion of the molecule containing the chelated metal either by direct conjugation or by a linker. To the imaging agent there could be attached a suitable linker to bond the imaging agent to a targeting agent. Suitable linkers include SMCC, succinic anhydride, and Di-Succinimdyl Suberate (DSS). To the linker there could be attached a suitable targeting agent for a biomarker.

An embodiment includes a method for transmetalation in which a PET or SPECT imaging agent containing a chelated metal is bound covalently or by non-covalent attractions such as lipophilic or hydrophilic attractions to a solid support or non-covalently bound to a solid support, such as those used in normal phase, reverse phase, ion exchange or affinity chromatography or solid supports used in peptide synthesis.

In particular, an embodiment includes a method of reversibly binding an imaging agent onto a reverse phase HPLC chromatography column where the binding is by a combination of lipophilic and ionic forces with no covalent bonding followed by transmetalation which is in turn followed by an elution step which can be combined with a purification step on the same column and in the same process as transmetalation using only a mixture of organic and aqueous based solvents to displace and purify the imaging agent for PET or SPECT.

There is provided practical methods for clinicians to easily prepare radioactive agents for PET or SPECT from non-radioactive precursor agents by transmetalation of place-holder metals.

An embodiment for construction of a targeted or non-targeted imaging agent includes chelating a labile place-holder metal, such as La, Ce, or Ba into a chelating group, such as DOTA, either early in the synthesis of an imaging agent or at a point in the synthesis after conjugation of a targeting group to the imaging agent.

In accordance with an embodiment, reactions such as deprotection reactions, coupling reactions, peptide chain extensions, additions of linkers, and conjugations to targeting groups can be accomplished while carrying the non-radioactive place-holder metal through the synthesis. In the synthesis the place-holder metal simultaneously acts as a protecting group for DOTA while at the same time providing a site for future chelation of a radioactive metal.

An embodiment includes a process whereby a targeted or non-targeted imaging agent containing a place-holder metal, such as La, Ce or Ba, may be transmetalated in the last step of the synthesis to provide a radionuclide metal for use in PET or SPECT imaging. This replacement can be accomplished via a direct trans-metalation or in a two-step process where the imaging agent containing the chelate and place-holder metal is de-metalized first to yield the unprotected DOTA itself, followed by re-metalation with the radioactive metal.

An embodiment includes a process utilizing a column commonly used for solid phase extraction (SPE), liquid chromatography (LC) or high pressure liquid chromatography (HPLC) and/or related apparatus in order to enhance the speed of transmetalation to accommodate the half-life timing requirements when using radioactive chemicals. This may be accomplished in a one step or two step transmetalation process. The disclosure extends to any metal-ligand group tethered through a carbon chain to an acid and/or amine group that can be conjugated to other imaging and/or targeting groups and easily displaced by mild acid in a one-step or two-step de-metalation and transmetalation methods. A feature of this approach is the ability to conjugate targeting biomolecules in the penultimate step of the synthesis. The labile place-holder lanthanide enables trans-metalation under mildly acidic conditions, by a radioactive metal such as copper (Cu) in the last step of the synthesis.

An embodiment includes a method for use of a column involving loading the precursor imaging agent onto the solid support, then transmetalation with a two-step procedure involving the flow of mild acid (such as 0.05, 0.1 or 0.2 M trifluoroacetic acid (TFA)) followed by a flow of a solution of the final radioactive metal of interest through the column, or a one-step procedure involving combining the mild acid and dilute radioactive metal solution to achieve the final radiolabeled imaging agent, followed by eluting the final product from one or two step procedure by changing the solvent so that the final product is achieved in under about a 24 hour time frame.

Figure 1:
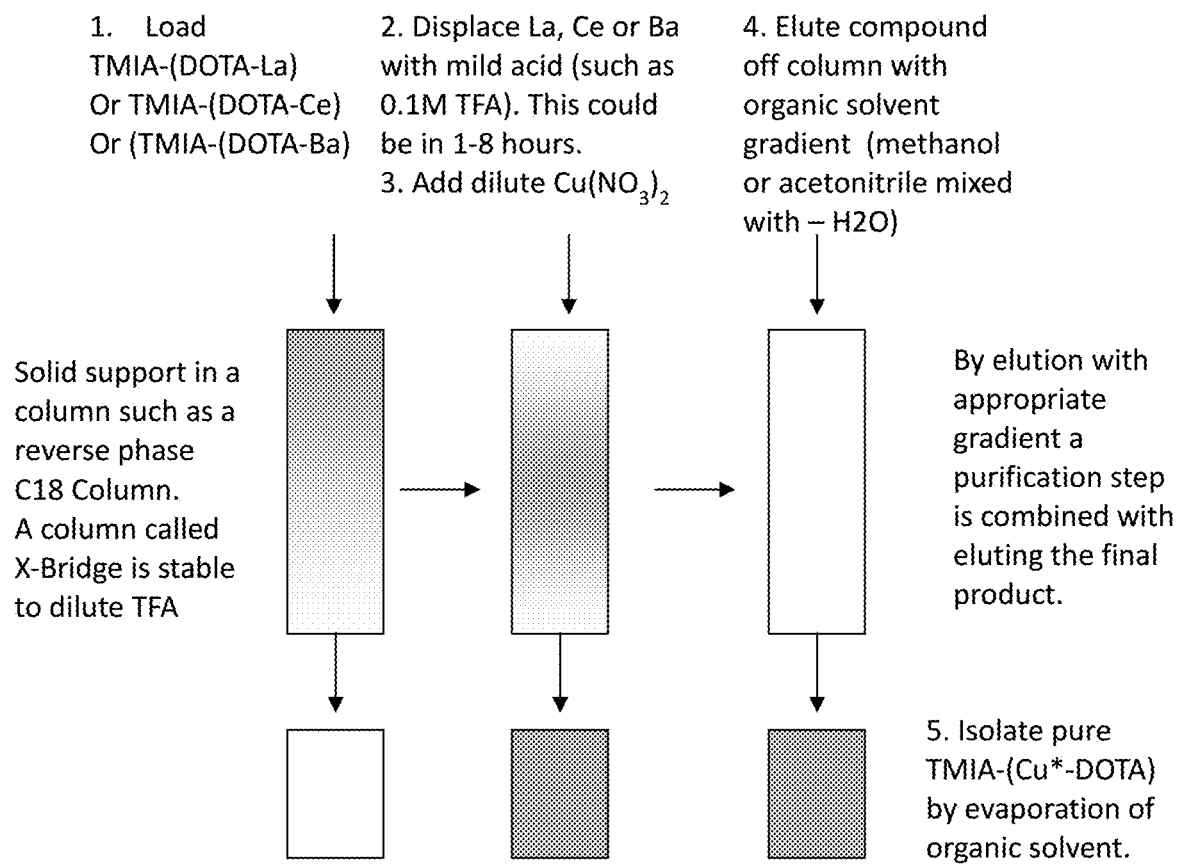
FIG. 1 is a flow chart depicting an embodiment of an apparatus for transmetalation of a chelated metal-TMIA complex on a solid support.

An embodiment of a process of the present disclosure is shown by illustration in FIG. 1. FIG. 1 illustrates an apparatus and process useful for the transmetalation of imaging agents for PET and SPECT utilizing a column containing a solid support and steps for displacement/replacement of a place-holder metal to a radioactive metal. FIG. 1 shows transmetalation of a chelated metal-TMIA complex on a solid support according to a Method 1 (two-step). A Method 2 (one-step) is identical except the Method 2 combines steps 2 and 3 of Method 1.

FIG. 2 illustrates Comparative Example A, which shows de-metalation in solution is slow compared to Methods 1 and 2 in accordance with the present disclosure. The mass spectra assay of the displacement of La from Fmoc-Lys (DOTA-La)—$NH_2$ (888.47 m/z) in 0.1 M TFA solution to form Fmoc-Lys(DOTA)-$NH_2$ (752.56 m/z) after one hour after start of de-metalation in solution, shows mostly starting material present and a very small amount converted to product). This de-metalation requires up to one week for completion.

Figure 3:
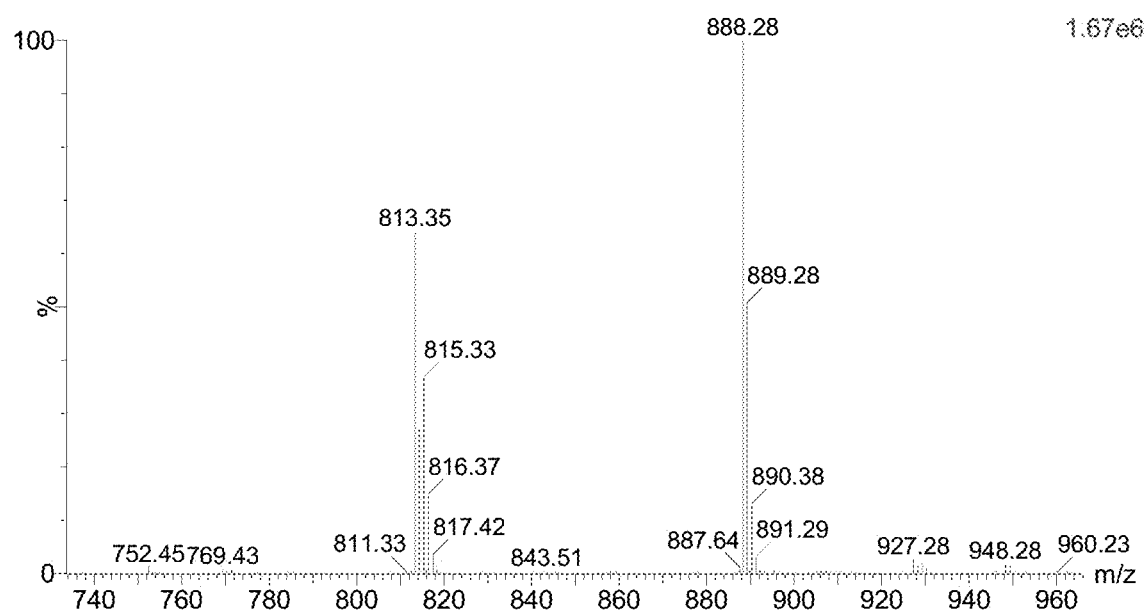
FIG. 3 is a mass spectra assay according to an example of the disclosed process.

FIG. 3 illustrates an example of an embodiment of the disclosed process, which shows acceleration of de-metalation on solid support. The mass spectra assay of the displacement and concomitant metal exchange using transmetalation Method 2 of Fmoc-Lys(DOTA-La)—$NH_2$ (888 m/z) to form Fmoc-Lys(DOTA-Cu)—$NH_2$ (813 m/z). The method was stopped after 1 hour, showing marked acceleration of transmetalation in progress relative to Comparative Example A. A similar result occurs using the two step transmetalation of Method 1.

Figure 4:
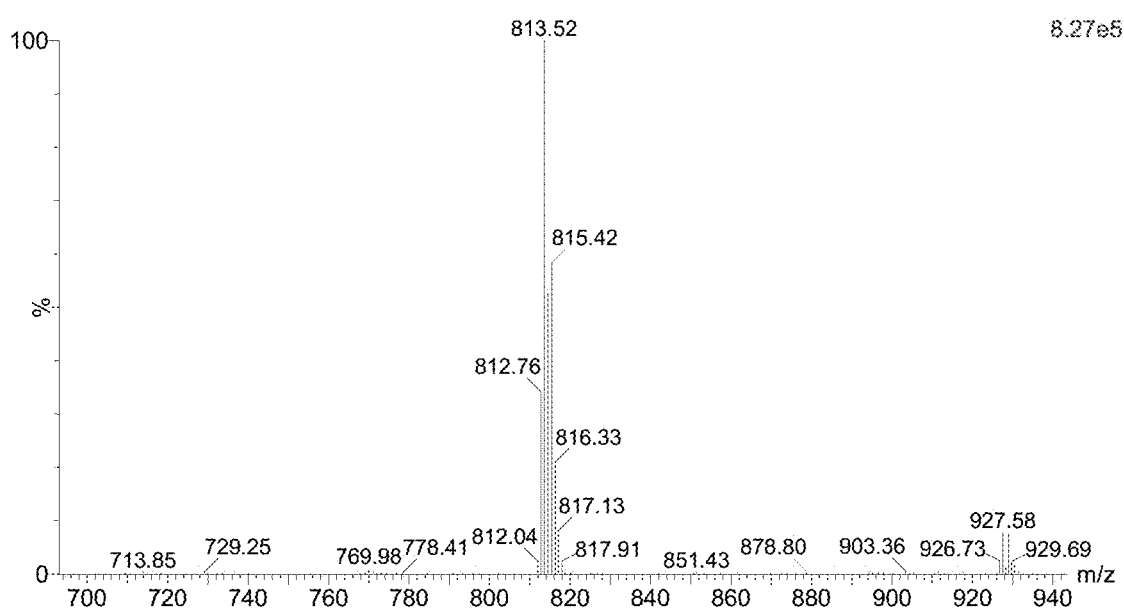
FIG. 4 is a negative ion mass spectra of Example 8.

FIG. 4 is a negative ion mass spectra of Fmoc-Lys (DOTA-Cu)—$NH_2$, the product of transmetalation on solid support of Example 8. Specifically, transmetalation of compound 6, Fmoc-Lys(DOTA-La)—$NH_2$ (888 m/z) to produce Example 8, Fmoc-Lys(DOTA-Cu)—$NH_2$ (813.52 m/z in negative ion mass spectra) utilizing Method 1 on an Xbridge C-18 HPLC column after 6 hours treatment with dilute 0.1 M TFA solution and dilute copper nitrate.

Figure 5:
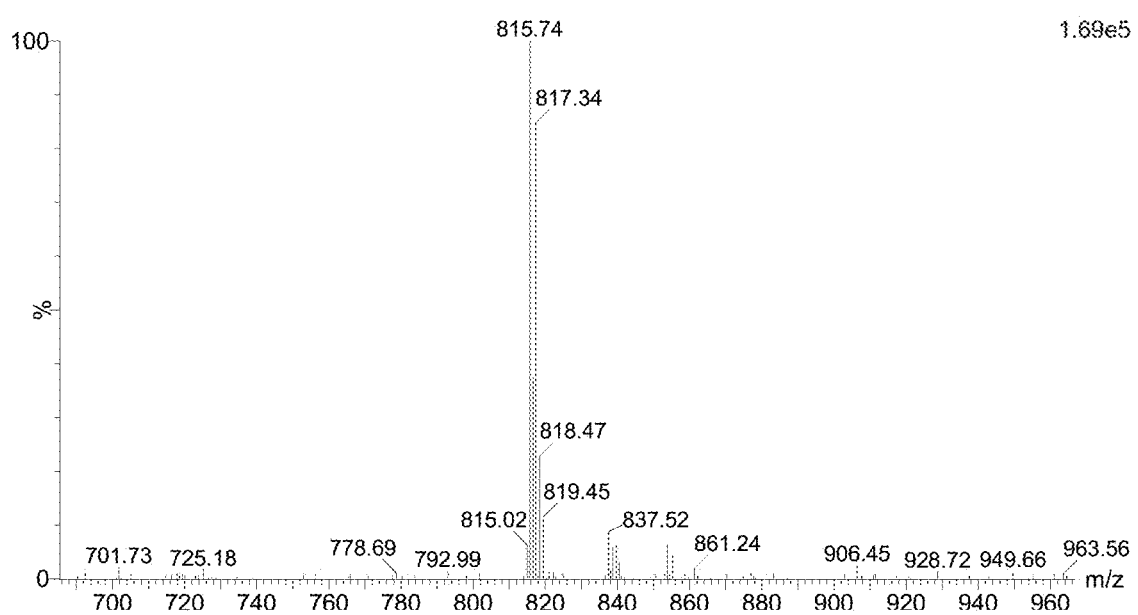
FIG. 5 is a positive ion mass spectra of Example 8.

FIG. 5 is a positive ion mass spectra of Fmoc-Lys(DOTA-Cu)—$NH_2$, the product of transmetalation on solid support of Example 8. Specifically, transmetalation of compound 4, Fmoc-Lys(DOTA-La)—$NH_2$ (888 m/z) to produce Example 8, Fmoc-Lys(DOTA-Cu)—$NH_2$, (815.52 m/z in positive ion mass spectra) utilizing Method 1 on an Xbridge C-18 HPLC column after 6 hours treatment with dilute 0.1 M TFA solution and dilute copper nitrate.

An embodiment includes a process of performing the transmetalation by the use of an HPLC pump, a reverse phase (C18) column, an isocratic or gradient elution, a fraction collector or other method of collecting fractions to markedly enhance the speed of reaction, which is desired when using radioactive chemicals with time limited half-lives, so that the one-step transmetalation or two step de-metalation followed by re-metallization can occur within a time frame conducive to detection techniques utilizing the half-life of the radioactive metal of interest.

In a preferred embodiment the optimized set of conditions employed was the use of a HPLC method in which the intermediate or penultimate peptide containing the place-holder metal, is adsorbed on a robust Xbridge C-18 column, designed for acid stability, followed by transmetalation on the HPLC column using 0.05 M TFA/0.005 M $Cu(NO_3)_2$ as the eluent in a one-step or two step procedure (TFA first, then $Cu(NO_3)_2$, followed by elution from the column with a 50% acetonitrile-water solution. With this optimized method, the Fmoc on protected peptide containing the La or Ce Fmoc-Lys(DOTA-La)—$NH_2$ was removed and replaced with a standard SMCC linker to yield SMCC-Lys(DOTA-La)—$NH_2$.

A versatile and practical method is provided for and exemplified by the transmetalation of imaging agents for PET, described below and shown in FIG. 1. A labile lanthanide metal, cerium (Ce), or lanthanum (La), barium (Ba) or strontium (Sr) is introduced early in the synthesis as both a place-holder and a protecting group for 1,4,7,10-tetraaza-cyclododecane-1,4,7,10-tetraacetic acid (DOTA) and is carried through the transmetalation under practical conditions.

By the use of this process various non-radioactive forms of either the targeted imaging agents for PET or activated imaging agents for PET containing a place-holder metal, could be transported with no encumbrances over great distances followed by conversion to the radioactive form of the imaging agent and subsequent purification in one process in the lab or clinic at the site where the radionuclide is prepared and/or utilized.

The method of transmetalation on a column, such as a reverse phase HPLC column, would be utilized to first enhance transmetalation, then purify the imaging agent after transmetalation for conversion to a radioactive imaging agent for PET or SPECT in the last step. The process would ideally be completed in a time frame of from about 1 to about 8 hours and include purification by chromatography in the last step. However, in the two step procedure the first mild, dilute acid step could occur over a longer 12-24 hour period followed by a very short (under 1 hour) treatment with radioactive metal, followed by elution by changing the solvent conditions either by a step or ramped gradient.

A metal exchange or transmetalation "kit" for creation of PET or SPECT agents from agents containing place-holder metals is disclosed. A "transmetalation kit" could be supplied to clinics, research hospitals or other such laboratories studying pre-clinical or clinical PET or SPECT agents. In the kit would be an HPLC column of the type described in the experimental section. Preferably this would be a small preparative column with diameter from 3 mm to 40 mm in diameter, and 30 to 300 mm in length, containing a C-18 or other suitable resin, and preferably one which would be stable to acid such as the X-bridge column chemistry. The reagents or recipes for all reagents described in the experimental section including TFA solutions, and non-radioactive Cu or Tc or other "cold" radioactive solutions could be included. The radioactive metals would be supplied by the clinic in most cases although under appropriate circumstances it could be supplied by the vendor of the kit. While an HPLC system including pump, injector, and detector and fraction collector would normally be supplied by a separate vendor, it could be supplied by the vendor of the "transmetalation kit". Complete directions for use would be supplied that could be applied to the transmetalation of intermediates or final imaging agents.

The disclosure will be further illustrated with reference to the following specific examples. It is understood that these examples are given by way of illustration and are not meant to limit the disclosure or the claims to follow.

EXAMPLES

As part of the HPLC method various column technologies were examined. The Waters XBridge column is an example of a column with reported stability to mild acid media and thus applicable to use for acid or matrix or acid and matrix assisted de-metalation or transmetalation.

It should follow that any metal complex from DOTA or the related analogs of NOTA, DPTA and others should be able to be performed on an HPLC column, with the complexes of La and Ce and La being among those most preferred for transmetalation to a radioactive metal such as those described above. This would include activated forms of DOTA-NHS esters and isocyanates similar to those that are commercially available, but containing La and Ce most preferably, and that any complex containing La and Ce could be transmetalated in an HPLC column by the use of mild acid and a transmetalation species such as Cu, Ga, Y, Zr, Tc, and In and other metals in their radioactive forms or mixed radioactive and non-radioactive (diluted in radioactivity) forms.

By the use of an HPLC column or preparative HPLC column and pump system, the equilibria may be shifted by virtue of Le Chatlier's principal by the use of flow of a dissolved, mild acid. This principal states that a reaction can be hastened or facilitated by the addition of a starting material or removal of a product from the reaction site. By immobilizing the imaging agent on a solid support, made possible by adherence of non-polar groups and polar groups in organic compounds to C-18 HPLC column packing, the continuous introduction of fresh acid for displacement of the metal while fresh radioactive metal (such as Cu) is present and the continuous removal of displaced metal (such as La or Ce) is occurring.

In this method the imaging agent containing a placeholder metal is loaded onto the HPLC column using pure or 95% aqueous conditions. The agent binds to the reverse phase packing material (C18) and mild acid (0.1 M TFA) is then pumped through the column for a requisite time, followed by neutralizing by pumping pure water. This is followed by employing a buffered solution of $Cu(NO_3)_2$ through the column, washing the column with water again and then retrieving the Cu imaging agent by eluting with a 10-50% gradient or isocratic 1:1 acetonitrile-water and concentrating followed by to the solid or to the desired strength thereby emulating formation of the final PET agent in a clinical or pre-clinical setting.

The analysis of the products from the preparative HPLC column by liquid chromatography-mass spectroscopy (LC-MS) by either method (two step or one step) clearly show the molecular masses for starting material and product, as shown in FIGS. 3-5.

This method of assembling a template, such as a peptide template, containing pre-formed amino acids with imaging groups on their side chains, has been optimized and applied to single modal PET agents, and has been applied to dual agents such as PET-MRI. The agents for PET-MRI are available from this route. This would also be applicable to other methods including PET-NIR, SPECT-NIR, PET-MRI, SPECT-PAI, SPECT-MRI and a variety of tri-modal agents including PET-NIR-MRI, NIR-SPECT-MRI or PET-PAI-MRI or SPECT-PAI-MRI.

A representative cancer-targeting peptide, integrin seeking c(RGDyK), was conjugated in the second to last step followed by metal exchange to provide two model Cu containing PET imaging agents: the direct conjugate c(RGDyK)-(DOTA-Cu) and a conjugate through linker and the reported modular lysine system, c(RGDyK)-SMCC-Lys(DOTA-Cu)—$NH_2$. A second peptide, the cholecystokinin derivative CCK4 was similarly conjugated to yield and CCK4-DOTA-Cu). Several other examples of targeted and non-targeted imaging agents are shown below.

The result is a widely applicable, practical synthetic approach enabling the versatile synthesis of PET agents utilizing standard conjugation which can be mixed with conditions of peptide synthesis and a wide variety of organic synthesis and purification conditions.

Structural types applicable to the disclosure include the following examples:

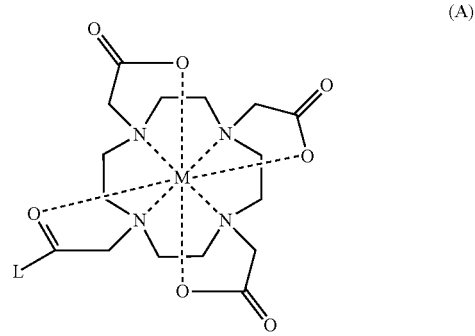

(A)

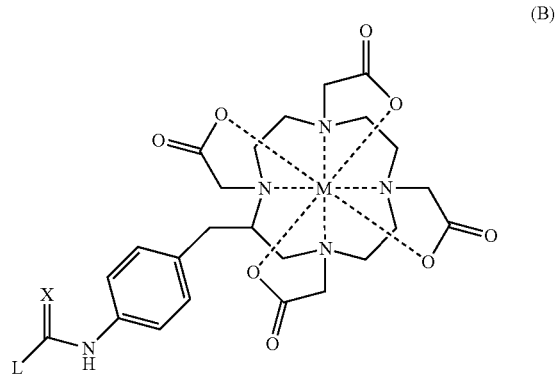

(B)

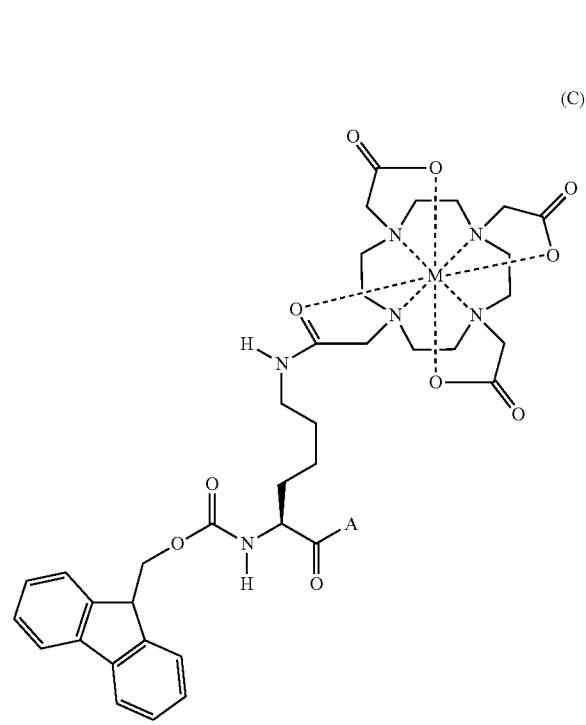

(C)

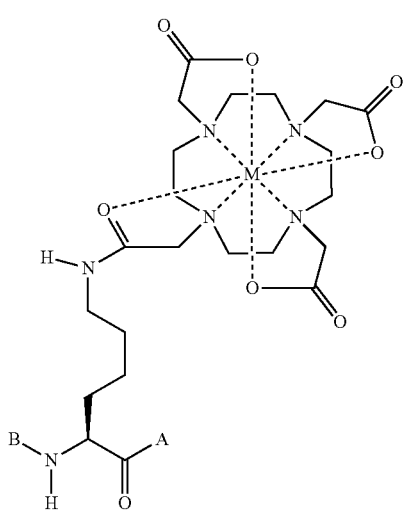

(D)

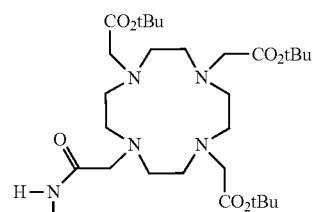

(2)
Fmoc—Lys(DOTA—OtBu)—NH₂

In structural types A and B the known chelating moiety DOTA is chelated to M, where M is a place-holder metal such as La, Ce, Ba, Sr, or Cs which may be exchanged to radioactive metals M' such as Cu, In, Tc, Ga and Y. Structural types C and D are disclosed in U.S. Patent Application Publication No. US 2015/0038672B where B may be H, protecting group, H, Peptide, Linker or Targeting agent or combinations of these and A is $NH_2$, OH or peptide chain extension.

Examples Numbered in the Order Listed in Experimental Section.

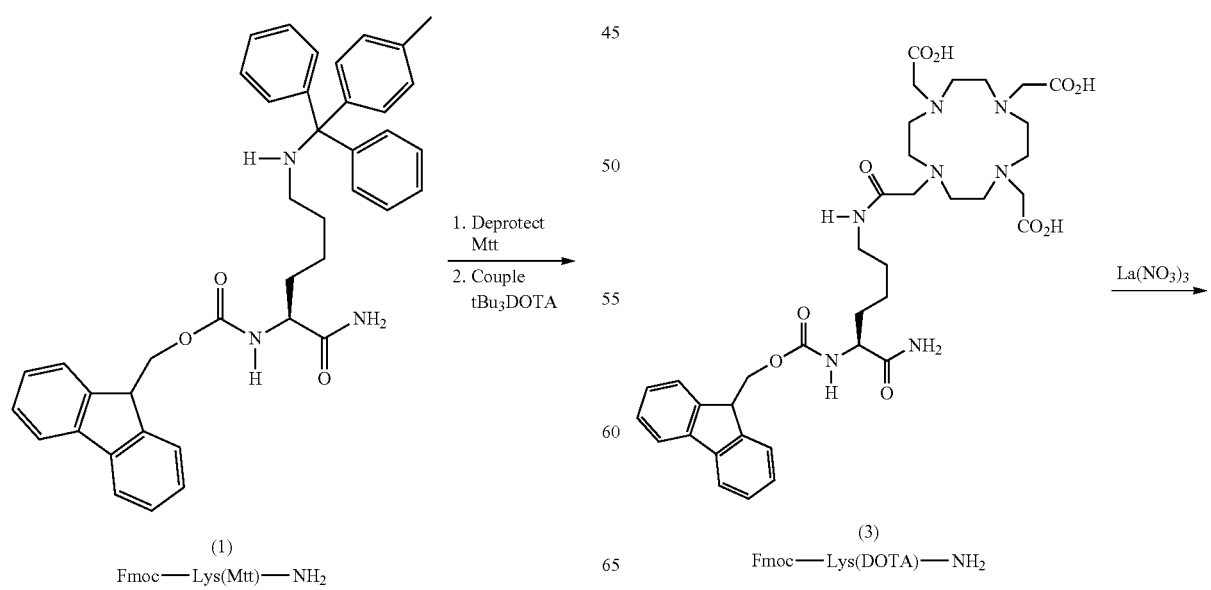

(1) Fmoc—Lys(Mtt)—NH₂

(3) Fmoc—Lys(DOTA)—NH₂

13
-continued
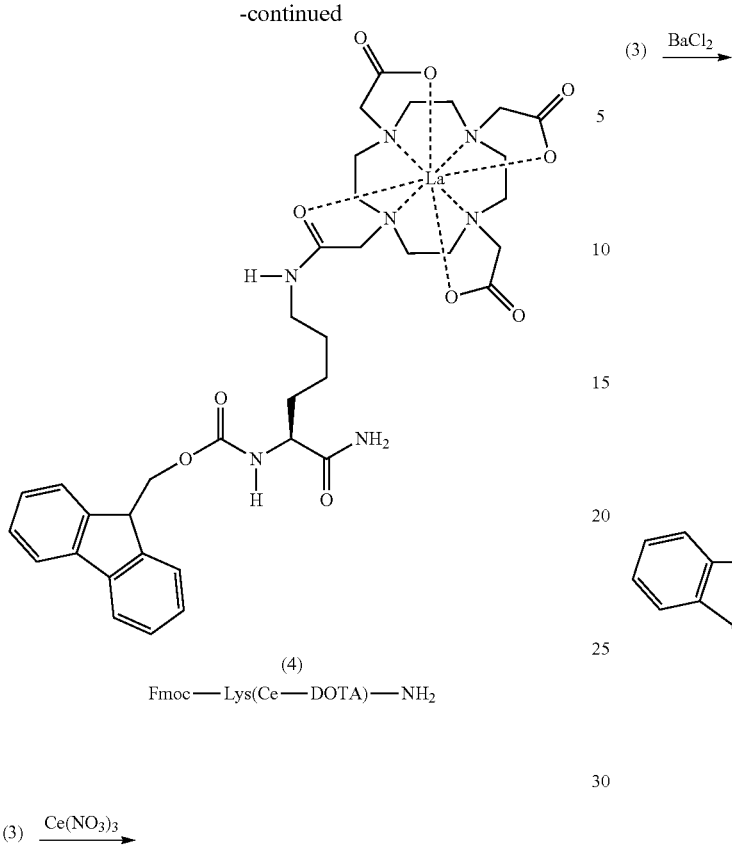
(4)
Fmoc—Lys(Ce—DOTA)—NH₂
(3) Ce(NO₃)₃ →
(5)
Fmoc—Lys(Ce—DOTA)—NH₂
14
-continued
(3) BaCl₂ →
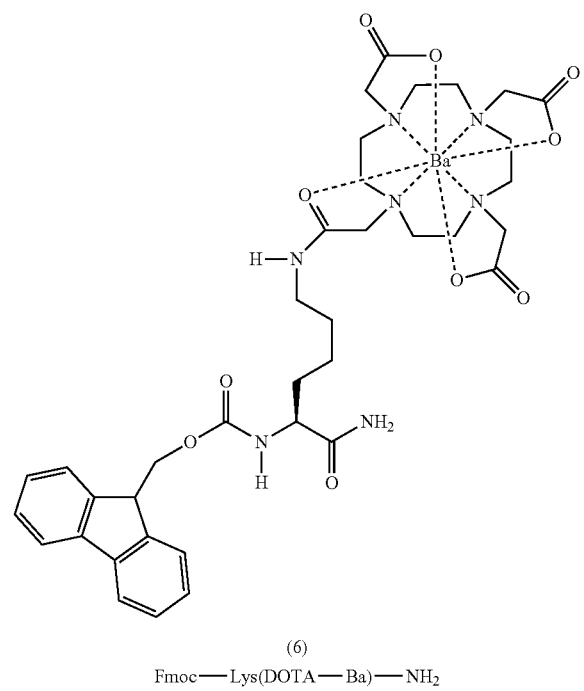
(6)
Fmoc—Lys(DOTA—Ba)—NH₂
(3) SrCl₂ →
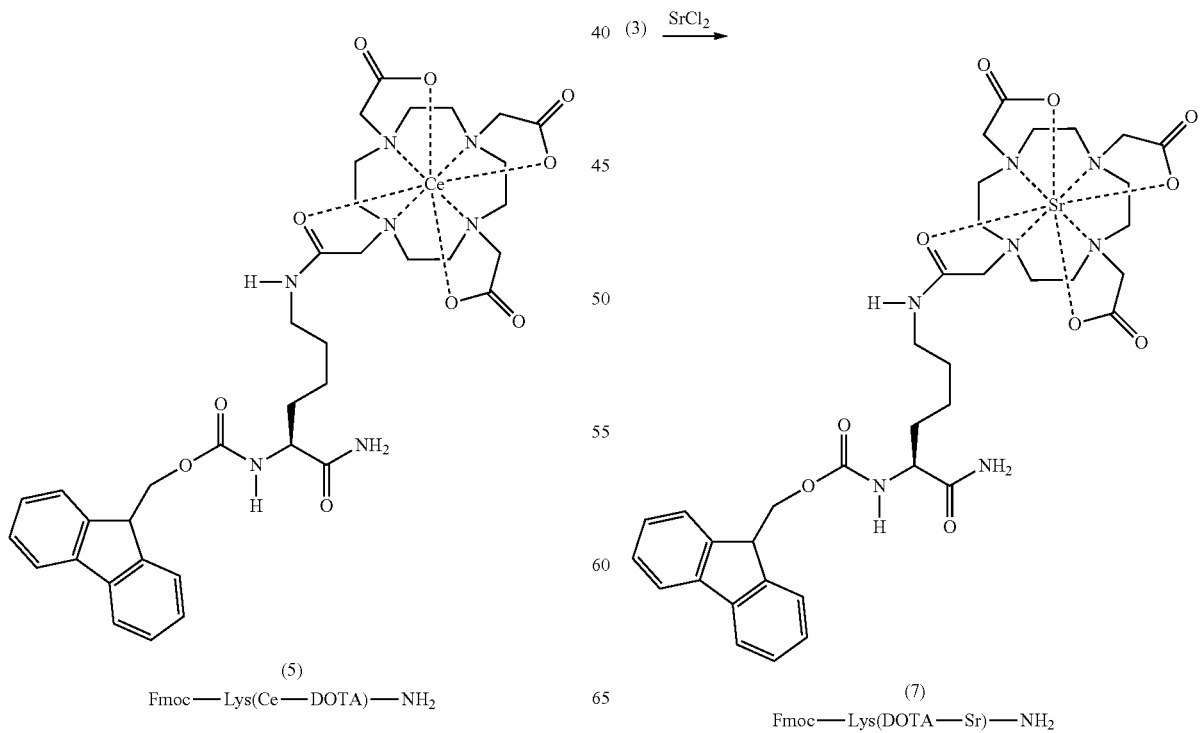
(7)
Fmoc—Lys(DOTA—Sr)—NH₂

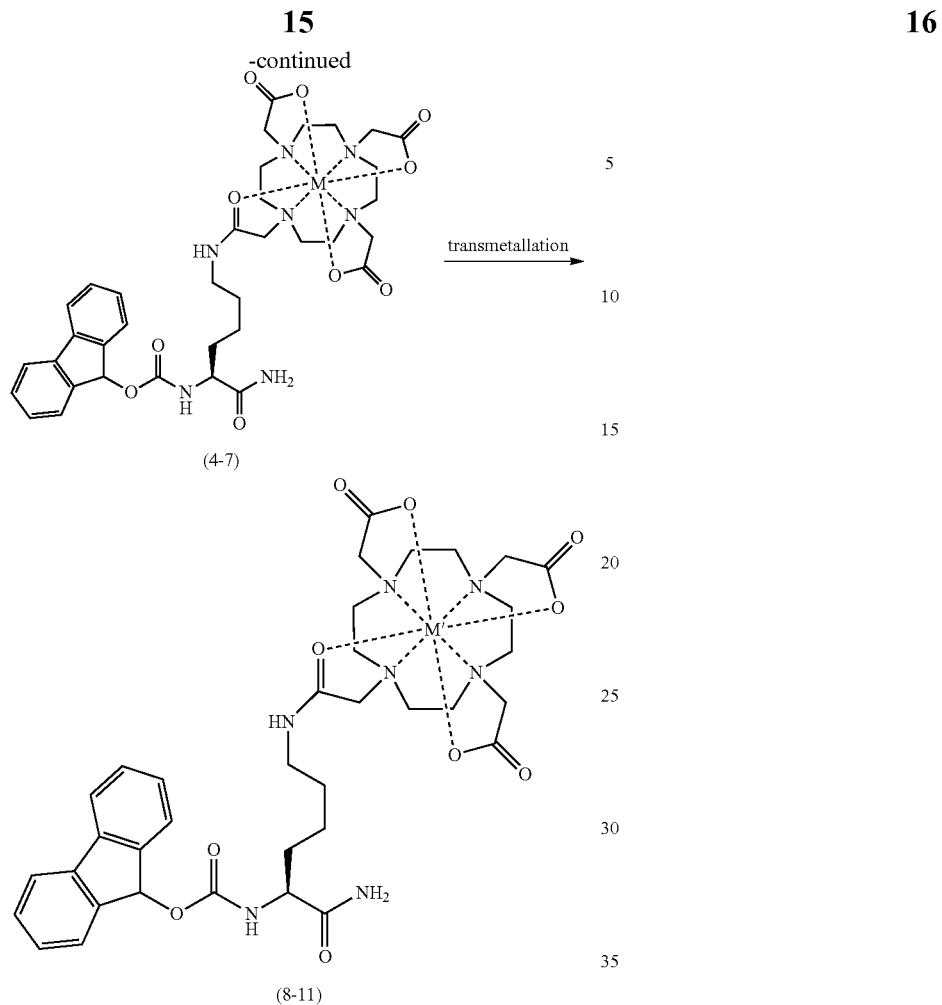
Where M=La (4), Ce (5), Ba (6), Sr (7), and M'=Cu (8); In (9), Ga (10), Y (11).
Application of Transmetalation in Targeted Molecular Imaging Agents (TMIAs):
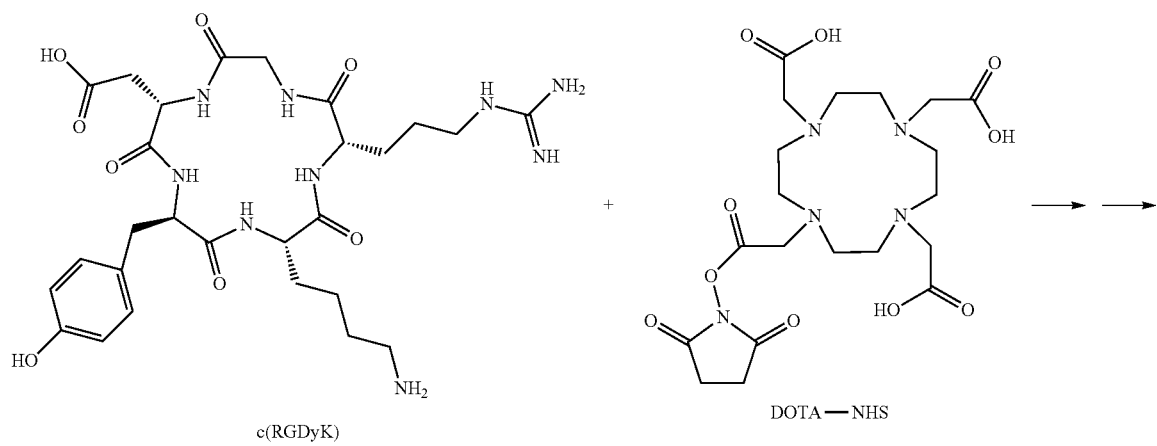

-continued
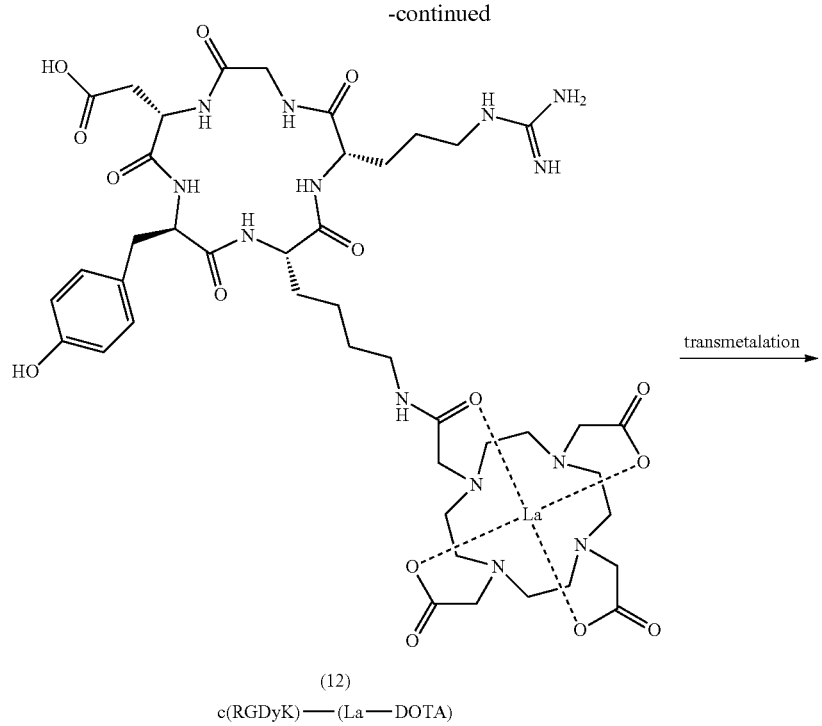
(12)
c(RGDyK)—(La—DOTA)
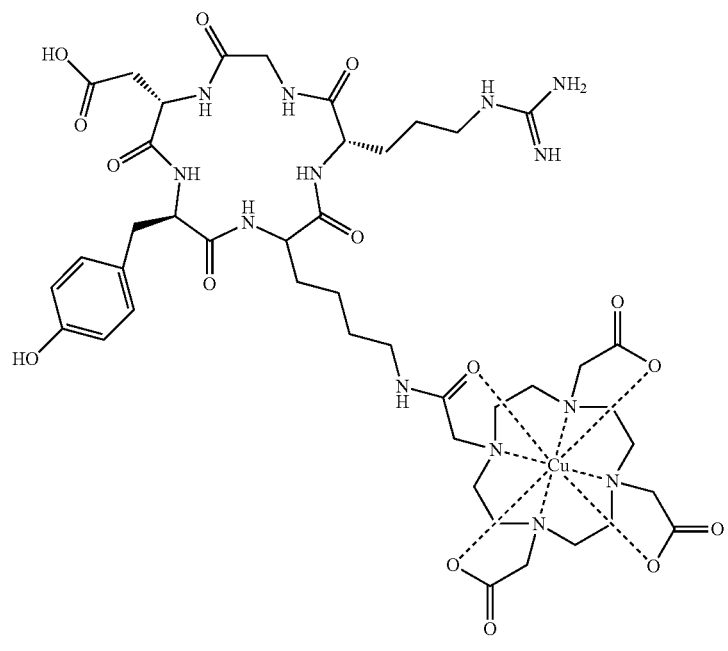
(13)
c(RGDyK)—(Cu—DOTA)

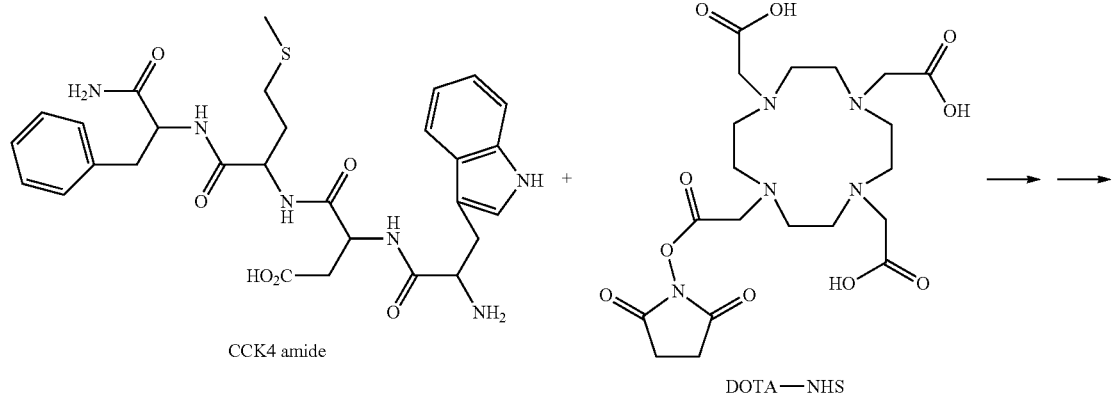
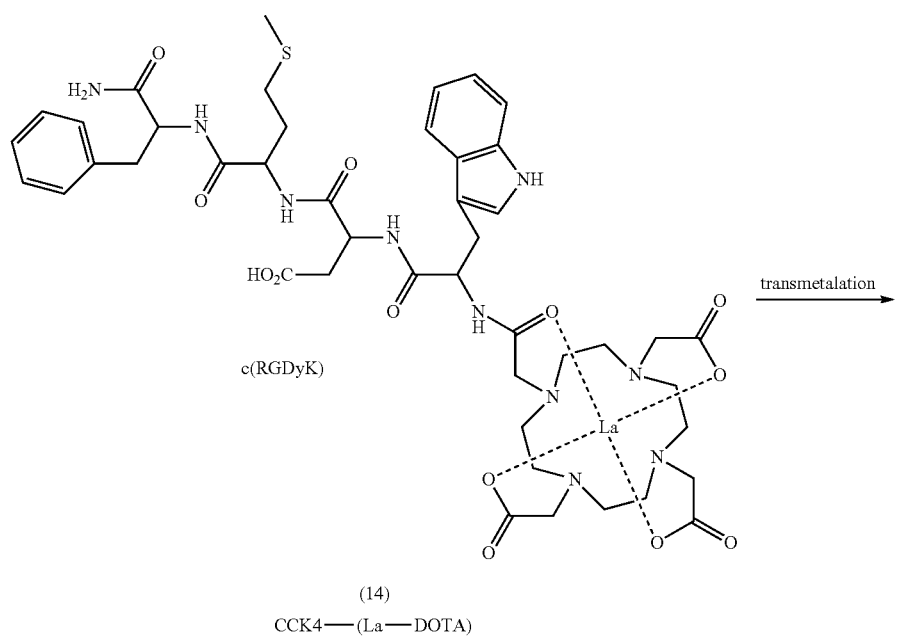
(14)
CCK4—(La—DOTA)
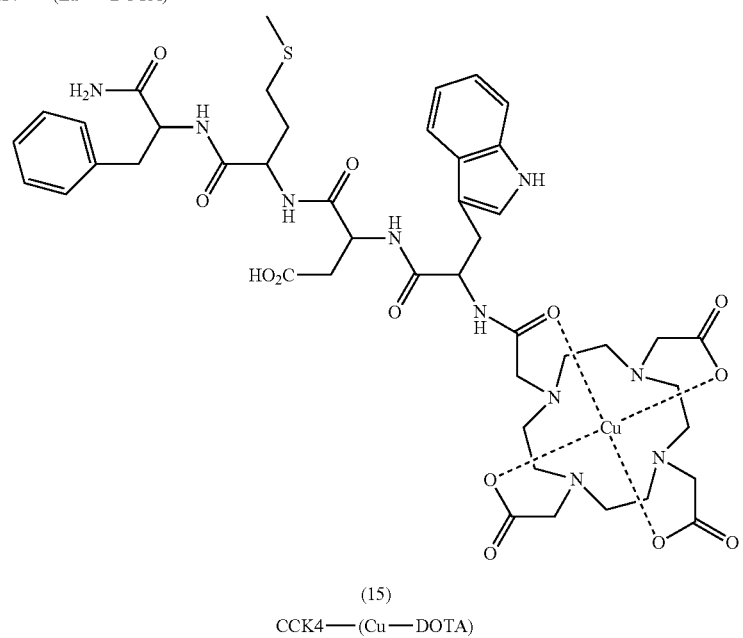
(15)
CCK4—(Cu—DOTA)

-continued
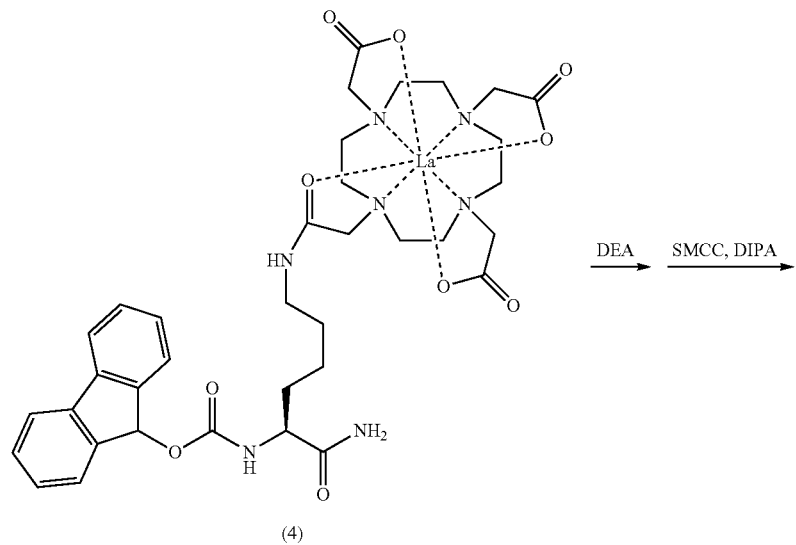
(4)
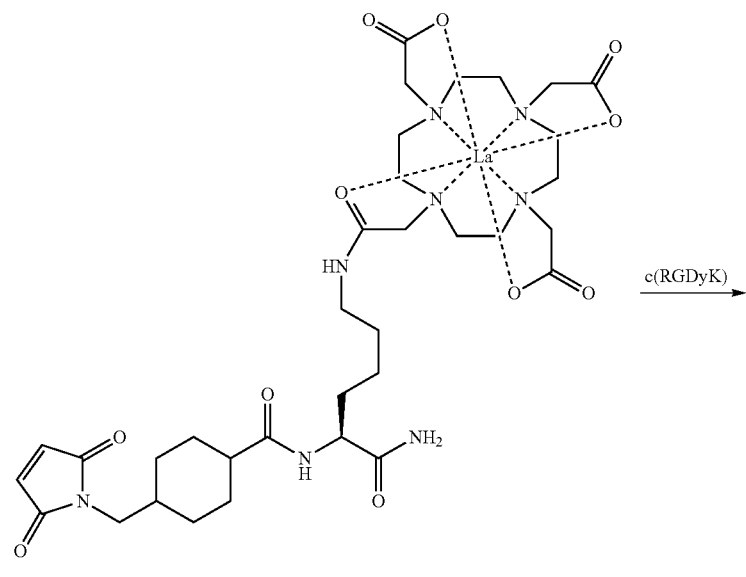
(16)

23                                            24
                                    -continued
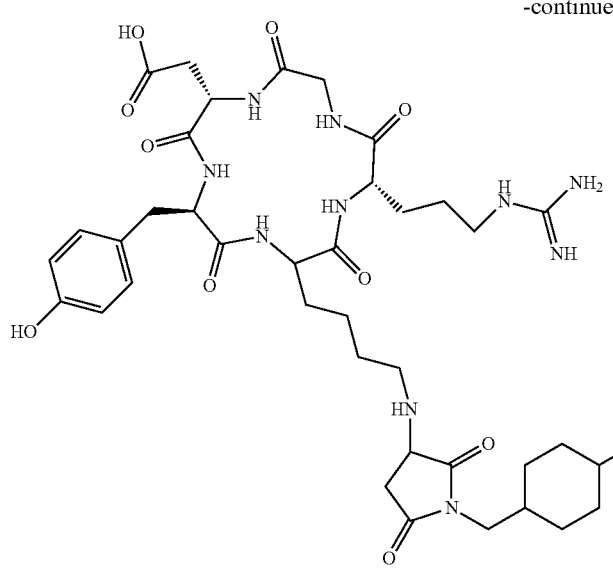
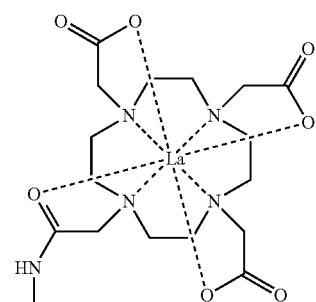
(17) transmetalation →
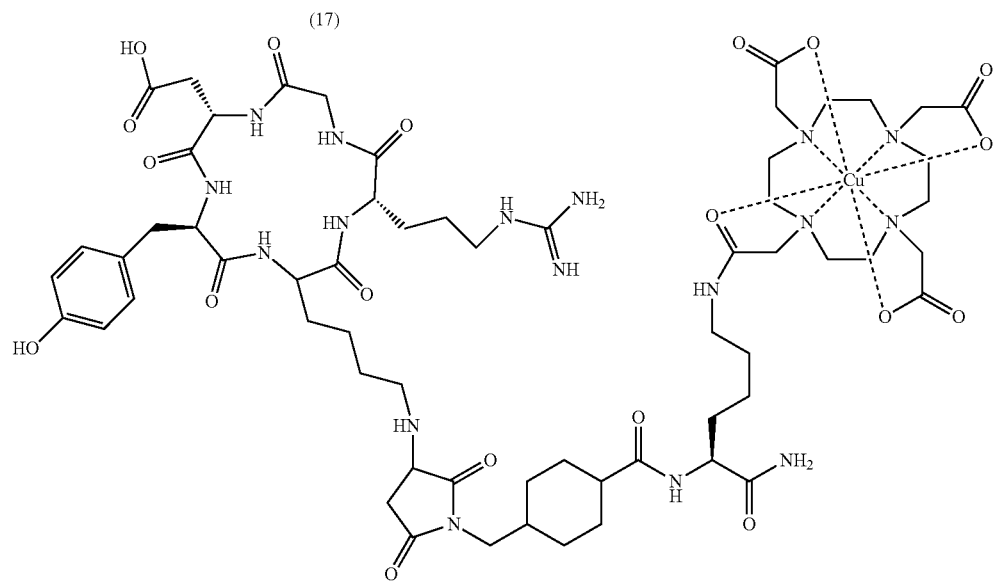
(18)
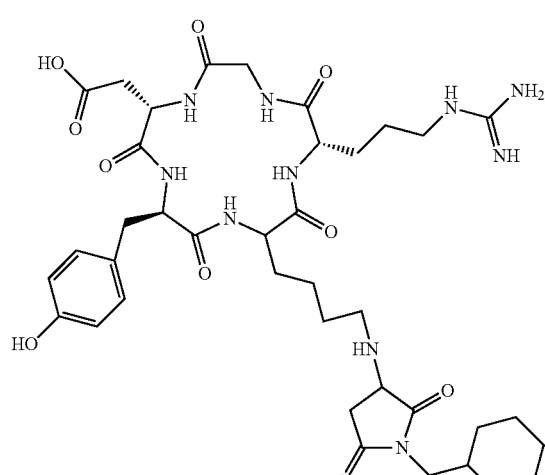
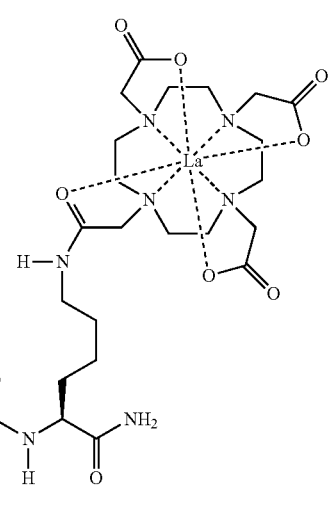
transmetalation →

-continued

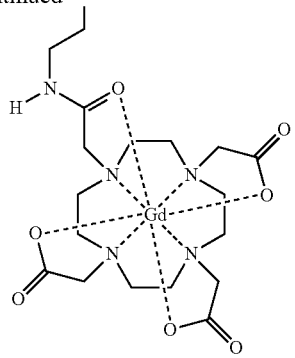

(19)

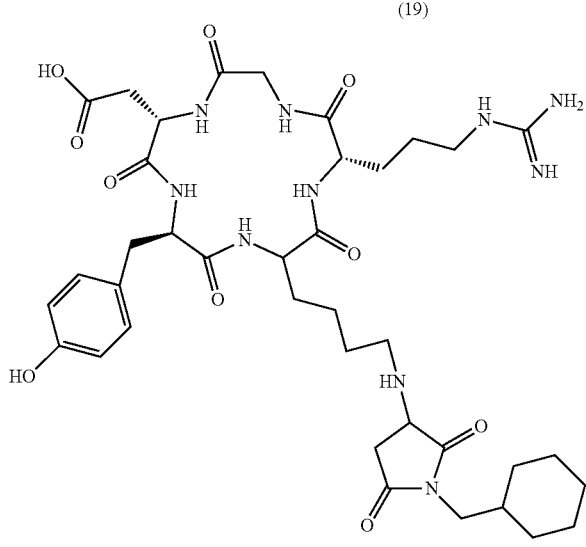

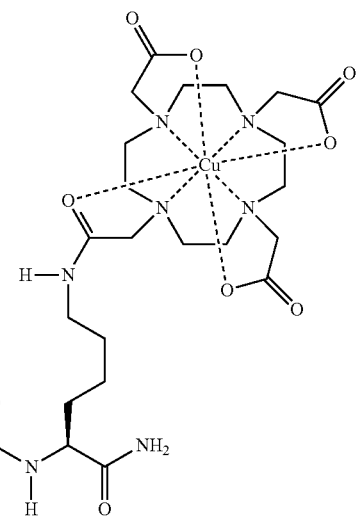

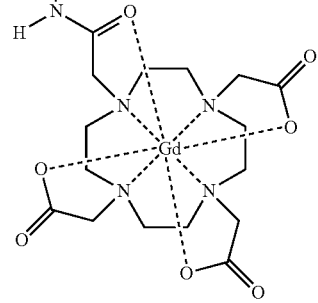

(20)

Experimental Section

Materials, Methods and Synthesis of Examples

Chemicals were purchased from Alfa Aesar (Ward Hill, Mass.) and were used as received unless otherwise stated. Fmoc-Lys(Mtt)-OH was purchased from Bachem (Bubendorf, Switzerland). 1,4,7,10-Tetraazacyclododecane-1,4,7-tris-(tert-butyl-acetate)-10-acetic acid (DOTA-tris (t-Bu) ester) was purchased from TCI. (Tokyo, Japan) or Macrocyclics (Houston, Tex.). The NMR ($^1$H, $^{13}$C, $^1$H-$^1$H COSY) data were obtained using a Bruker Avance III 500 MHz NMR spectrometer and chemical shifts as δ are reported in ppm relative to TMS. The HPLC instrument used for HPLC was an Agilent 1100 with Diode Array Detector and for LC-MS a Waters 2695 Alliance HPLC with a Waters 2998 Diode Array Detector and an Agilent XDB C18 column, Waters Sunfire C18 with dimensions of 3 mm by 100 mm or a Waters XBridge C18 column 3 mm by 50 MM and 3 micron particle size. For transmetalation a Waters XBridge C18 column 10 mm by 50 MM and 5 micron particle size was also utilized. Mass spectral data were collected using both positive and negative modes on a Waters 3100 SQ Mass Spectrometer. The flow rate was 0.5 mL/min with the mobile phase gradient starting at 90% solvent A (0.1 M ammonium acetate buffer) and 10% solvent B (acetonitrile or methanol) to 0% solvent A and 100% solvent B at 8 minutes, or from 30% B to 70% B in the case of kinetic studies. References to Method A: X % indicate acetonitrile starting at X % and in method B: X % indicate staring methanol at X %. For purification, a 20 g C-18 Sep-pack ((Varian Mega Bond Elut 20CC/5GRM)) SPE cartridge was utilized. The cartridge was conditioned with acetonitrile, then pure DI water then 5% A, followed by loading the dissolved product and a step gradient of acetonitrile 10-100% in 5% increments with 3-10 mL fractions each. Common solvents and reagents used were dimethyl formamide (DMF), n-methyl pyrolidone (NMP), n-methyl morpholine (NMM), and diisopropyl-ethlamine (DIPA). Common coupling agents of conventional use in peptide synthesis include TBTU, HATU and TSTU. Common linkers include SMCC and DSS. It should be noted that procedures on a scale less than 10 mg may incur substantial losses in yield from aliquots taken for LC-MS and other analyses.

Synthetic Methods

Compound (1): Synthesis of Fmoc-Lys(Mtt)-NH$_2$. Solid Fmoc-Lys(Mtt)-OH (1 g, 1.6 mmol, Bachem) was dissolved in DCM (50 mL). Added in quick succession were HOBt (43.3 mg, $3.20 \times 10^{-1}$ mmol), DIPA (620 mg, 4.80 mmol), and TBTU (617 mg, 1.92 mmol). After 5 minutes, 30% ammonia (294.4 mg, 5.76 mmol) was added to the solution. The reaction was monitored every 0.5 hour via TLC (50:50 mixture of EtAc:Hexanes). The reaction was run for 1 hour. The solution was rotary evaporated and dried under high vacuum. Purification was done by extraction using DCM versus potassium sulfate, sodium carbonate, and sodium chloride with a sequential back extraction of aqueous layers with a single DCM layer. The product in organic phase was rotary evaporated and dried under high vacuum to yield off-white foam. The yield was 934 mg (93.6%). LC-MS=Calcd. for $C_{41}H_{41}N_3O_3$: 623.8 found: 624.6 [M+H]$^+$.

Compound (2): Fmoc-Lys(DOTA-OtBu)-NH$_2$. The next step removed the Mtt group to form Fmoc-Lys(H)—NH$_2$. A solution of Fmoc-Lys(Mtt)-NH$_2$ (500 mg, $8.0 \times 10^{-1}$ mmol) in DCM (5 mL) was cooled to 4° C. in an ice bath. Once removed from the ice bath, TFA (0.5 mL, 10%) was added to the cooled down solution. The mixture was then stirred for 0.5 hour and was monitored via HPLC method A: 20-100% every 0.25 h. The reaction was run for 1 hour in total. The solution was rotary evaporated and dried under high vacuum. Purification was done through SPE using methanol: 5-70%. The fractions were tested in the LC-MS with the same method utilized for the reaction. Pure product was found in fractions 30-40%. These fractions were combined, rotary evaporated, and dried under high vacuum. The yield was 280 mg (95.2%).

The commercially available DOTA-tris (t-Bu ester) was then coupled to the Fmoc-Lys(H)—NH$_2$ using the following steps. The solid Fmoc-Lys(H)—NH$_2$ (60 mg, $1.63 \times 10^{-1}$ mmol) was heated in a 50:50 solution of DCM:DMF (6 mL) to dissolve the solid. Separately, the solid DOTA-tris (t-Bu ester) (112.23 mg, $1.96 \times 10^{-1}$ mmol) was dissolved in pure DCM (5 mL). To the dissolved DOTA-tris (t-Bu ester) (4.41 mg, $3.27 \times 10^{-2}$ mmol), TBTU (62.92 mg, $1.96 \times 10^{-1}$ mmol), and DIPA (84.42 mg, $6.53 \times 10^{-1}$ mmol) were added. These two separate solutions were then combined and the reaction was monitored every 0.5 hour through LC-MS method A: 20-10$^{-1}$%. The reaction was run for 3.5 hour. The solution was rotary evaporated and dried under high vacuum. Purification was done via extraction using EtOAc and water with a sequential back extraction of aqueous layers with a single EtOAc layer. The product in organic phase was rotary evaporated and dried under high vacuum. The yield was 103.5 mg (68.73%). LC-MS=Calcd. for $C_{49}H_{75}N_7O_{10}$: 922.6 (m/z). found: 921.9 [M–H]$^-$.

Compound (3): Fmoc-Lys(DOTA)-NH$_2$. To a solution of Fmoc-Lys(DOTA-OtBu)-NH$_2$ (247.1 mg, $1.34 \times 10^{-1}$ mmol) in pure TFA (3 mL), 6 drops of deionized water was added (2 drops per 1 mL of TFA). The solution was stirred for 3.5 hour at room temperature while using LC-MS method A: 50-100% to check the reaction progress every 0.5 hour. Once the reaction was complete, the material was rotary evaporated, dried under high vacuum, and used without further purification in the subsequent step. The yield was 100.3 mg (83.0%). LC-MS=Calcd. for $C_{37}H_{51}N_7O_{10}$: 753.4 (m/z). found: 752.7 [M–H]$^-$, 754.5 [M+H]$^+$.

Compound (4): Fmoc-Lys(DOTA-La)—NH$_2$. Fmoc-Lys (DOTA)-NH$_2$ (200.0 mg, $2.65 \times 10^{-1}$ mmol) was added to a 100 mL round bottom flask and dissolved in 6 mL of 0.5 M sodium acetate. La(NO$_3$)$_3$ (230.6 mg, $5.33 \times 10^{-1}$ mmol) was measured out in a 20 mL vial, dissolved in 2 mL of 0.5 M sodium acetate, and transferred to the round bottom flask. The solution was stirred for 30 minutes at room temperature while using LC-MS method A: 20-100% to check the reaction progress. Purification was done through SPE using acetonitrile: 5-70%. The fractions were tested in the LC-MS with the same method utilized for the reaction. Pure product was found in fractions 25-45%. These fractions were combined, rotary evaporated, and dried under high vacuum. The yield was 111.2 mg (48.13%). LC-MS=Calcd. for $C_{37}H_{48}N_7O_{10}La$: 889.25 (m/z). found: 888.38 [M–H]$^-$, 890.27 [M+H]$^+$.

Compound (5): Fmoc-Lys(DOTA-Ce)—NH$_2$. Fmoc-Lys (DOTA)-NH$_2$ (50.0 mg $6.63 \times 10^{-2}$ mmol) was added to a 50 mL round bottom flask and dissolved in 1.5 mL of 0.5 M sodium acetate. Ce(NO$_3$)$_3$ (94.01 mg, $2.16 \times 10^{-1}$ mmol) was measured out in a 20 mL vial, dissolved in 0.5 mL of 0.5 M sodium acetate, and transferred to the round bottom flask. The solution was stirred for 30 minutes at room temperature while using LC-MS method A: 20-100% to check the reaction progress. Purification was done through SPE using acetonitrile: 5-70%. The fractions were tested in the LC-MS with the same method utilized for the reaction. Pure product was found in fractions 25-30%. These fractions were combined, rotary evaporated, and dried under high vacuum. The yield was 31.2 mg (56.63%). LC-MS=Calcd. for $C_{37}H_{49}N_7O_{10}Ce$: 890.25 (m/z). found: 889.34 [M–H]$^-$, 891.35 [M+H]$^+$.

Compound (6): Fmoc-Lys(DOTA-Ba)—NH$_2$. Fmoc-Lys (DOTA)-NH$_2$ (5.0 mg $6.63 \times 10^{-3}$ mmol) was converted by the identical procedure as in Example 5 using Ba(Cl)$_2$ and SPE to produce the product. The yield was 3.0 mg (50.9%). LC-MS=Calcd. for $C_{37}H_{49}N_7O_{10}Ba$: 888.25 (m/z). found: 888.38 [M-]$^-$, 890.27 [M+2H]$^+$.

Compound (7): Fmoc-Lys(DOTA-Sr)—NH$_2$. Fmoc-Lys (DOTA)-NH$_2$ (5.0 mg, $6.63 \times 10^{-3}$ mmol) was converted by the identical procedure as in Example 5 using Sr(Cl)$_2$ and SPE to produce produce the product. The yield was 3.1 mg (55.7%). Calcd. for $C_{37}H_{48}N_7O_{10}Sr$: 838.44 (m/z). found: 838.30 [M–H]$^-$, 840.34 [M+H]$^+$.

De-metalation and transmetalation kinetic studies. Utilizing the solution methods reaction kinetics were measured on dilute solutions of Examples 4 and 5 in a variety of acid strengths including 0.05, 0.1, 0.2, 0.3, 0.4, and 0.5 M TFA using analytical LC-MS to monitor the reactions. Representative runs showed that in solution the transmetalation typically required days instead of hours. However, they also showed that while La and Ce may be displaced and transmetalated, Eu and Gd are stable under these conditions during the entire length of time, even at the higher acid strengths. The acid strength of 0.1 M in TFA was chosen as optimal for the subsequent accelerated transmetalation methods in Methods 1 and 2 described below. This was ideal for stability of many biologically derived targeting groups and it also matched to the range of stability in acid strength reported for the X-Bridge column support.

Method 1: Two step transmetalation process on solid support: Exemplified by the synthesis of Compound (8) Fmoc-Lys(DOTA-Cu)—NH$_2$. The apparatus consisted of a Waters 590 HPLC pump, LabPro Switching Valve, Waters XBridge C18 3.5 µm 3.0×50 mm column, and fraction collector. To exemplify this exchange, the modular intermediate Fmoc-Lys(DOTA-La)—NH$_2$ was tested and a solution of 5% MeOH and 0.1 M TFA was used to promote the displacement of the place-holder metal, La. To start, the HPLC column was conditioned by running acetonitrile for 10 minutes and then HPLC grade water was run for 10 minutes at 4 mL/min. The Fmoc-Lys(DOTA-La)—NH$_2$ (3.0 mg) dissolved in 1 mL of HPLC grade water was injected into the LabPro Switching Valve, then was loaded onto the column. The solution of 5% MeOH and 0.1 M TFA was run at 4 mL/min through the column for four hours. The column was neutralized by running HPLC grade water until a strip of pH paper indicated the solution coming from the column was at a pH of 6. A solution of 20 mL of 0.032 M Cu(NO$_3$)$_2$ in 0.25 M sodium acetate was run for 5 minutes to create the model PET intermediate Fmoc-Lys(DOTA-Cu)—NH$_2$. Once the Cu(NO$_3$)$_2$ solution was consumed, HPLC grade water was run for about 10 minutes to remove any excess Cu from the column. The Fmoc-Lys(DOTA-Cu)—NH$_2$ was removed from the column by running 50% acetonitrile and collecting fractions coming off the column every 2 minutes, resulting in about 8 mL collected per tube. The fractions collected were tested on the HPLC-MS. LC-MS results indicated that there was complete conversion from Fmoc-Lys(DOTA-La)—NH$_2$ (888 m/z) to Fmoc-Lys(DOTA-Cu)—NH$_2$ (813 m/z). Tubes containing Fmoc-Lys(DOTA-Cu)—NH$_2$ were combined and concentrated by rotary evaporation and freeze drying to yield 2.0 mg of the product as a white fluffy solid. LC-MS=Calcd. for C$_{37}$H$_{48}$CuN$_7$O$_{10}$: 813.3 (m/z). found: 813.4[M]$^-$, 815.3 [M+H]$^+$ Method 2: One step transmetalation process on solid support: Exemplified by the synthesis of Compound (8) Fmoc-Lys(DOTA-Cu)—NH$_2$. The method described in Method 1 was applied with the difference being the simultaneous addition of the metal to be exchanged, in this case a dilute solution of Cu$^{2+}$ with the dilute solution of TFA acid. Fmoc-Lys(DOTA)-NH$_2$, was transmetalated by loading onto the column as in Method 1. The HPLC column was first conditioned by running acetonitrile for 10 minutes and then a solution of 5% MeOH and HPLC grade water was run for 10 minutes at 4 mL/min. The Fmoc-Lys(DOTA-La)—NH$_2$ (3.0 mg) dissolved in 1 mL of HPLC grade water was injected into the LabPro Switching Valve, then was loaded onto the column. The solution of 5% MeOH, 0.1 M TFA and 0.4808 g Cu(NO$_3$)$_2$ was run at 4 mL/min through the column for four hours. The column was neutralized by running the solution of 5% MeOH and HPLC grade water until a strip of pH paper indicated the solution coming from the column was at a pH of 6. The Fmoc-Lys(DOTA-Cu)—NH$_2$ was removed from the column by running 50% acetonitrile and collecting fractions coming off the column every 2 minutes, resulting in about 8 mL collected per tube. The fractions collected were tested on the HPLC-MS. Results indicated that there was complete conversion from Fmoc-Lys(DOTA-La)—NH$_2$ (888 m/z) to Fmoc-Lys(DOTA-Cu)—NH$_2$ (813 m/z). Tubes containing Fmoc-Lys(DOTA-Cu)—NH$_2$ were combined and concentrated by rotary evaporation and freeze drying to yield 2.0 mg of the product as a white fluffy solid. LC-MS=Calcd. for C$_{37}$H$_{48}$CuN$_7$O$_{10}$: 813.3 (m/z). found: 813.4[M]$^-$, 815.3 [M+H]$^+$.

Compound (9): Fmoc-Lys(DOTA-In)—NH$_2$. This model agent for PET was prepared from Fmoc-Lys(DOTA-La)—NH$_2$, (4) on a 1.0 mg scale by the two-step Method 1 utilizing the indium (In) complex In(XXX)$_x$ to yield 0.7 mg Fmoc-Lys(DOTA-In)—NH$_2$ after purification in the same column LC-MS=Calcd. for C$_{37}$H$_{48}$N$_7$O$_{10}$In: 865.64 (m/z). found: 924.45 [M+acetic acid adduct], 866.37 [M+H]$^+$.

Compound (10): Fmoc-Lys(DOTA-Ga)—NH$_2$. This model agent for PET was prepared from Fmoc-Lys(DOTA-La)—NH$_2$, (4) on a 1.0 mg scale by the two-step Method 1 utilizing the gallium (Ga) complex In(XXX)$_x$ to yield 0.5 mg Fmoc-Lys(DOTA-Ga)—NH$_2$ after purification in the same column LC-MS=Calcd. for C$_{37}$H$_{48}$N$_7$O$_{10}$Ga: 819.27 (m/z). found: 878.36 [M–H Acetic Acid Adduct]$^-$, 820.34 [M+H]$^+$.

Compound (11): Fmoc-Lys(DOTA-Y)—NH$_2$. This model agent for PET was prepared from Fmoc-Lys(DOTA-La)—NH$_2$, (4) on a 1.0 mg scale by the two-step Method 1 utilizing the yttrium (Y) complex Y(XXX)$_x$ 3 to yield 0.7 mg Fmoc-Lys(DOTA-In)—NH$_2$ after purification in the same column LC-MS=Calcd. for C$_{37}$H$_{48}$N$_7$O$_{10}$Y: 839.72 (m/z). found: 838.34 [M–H]$^-$, 840.4 [M+H]$^+$.

Compound (12): c(RGDyK)-(DOTA-La). To a solution of NHS-DOTA (Macrocyclics), (2.0 mg, 3.14×10$^{-3}$ mmol) dissolved in NMP (1.0 mL), the targeting peptide c(RGDyK) (Peptides, International) (1.95 mg, 3.14×10$^{-3}$ mmol) in NMP (1.0 mL) with DIPA (4.07 mg, 3.15×10$^{-2}$ mmol) and TSTU (1.90 mg, 6.30×10$^{-3}$ mmol) was added. The solution was stirred for 4 h at room temperature while using LC-MS method B: 5-100% to check the reaction progress. Once the reaction was complete, the solid La(NO$_3$)$_2$ (3.41 mg, 7.87 mmol) was added, again following by LC-MS method B: 5-100% to check the reaction progress which was immediate. Diethyl ether (5 mL) was added to precipitate the product which was vortexed and centrifuged in a 15 mL centrifuge tube This product was purified through SPE using method B: 5-50% with product found in fractions 5-20%. Yield: 1.2 mg (1.03×10–3 mmol, 50.5%); LC-MS=Calcd. for C$_{43}$H$_{64}$LaN$_{13}$O$_{15}$: 1141.37 (m/z). found: 1140.40 [M–H]–; 570 [(M–2H/2]$^-$.

Compound (13): c(RGDyK)-(DOTA-Cu). A solution of c(RGDyK)-Lys(DOTA-La), (10) (0.5 mg, 0.44××10-4 mmol) was transmetalated by the two-step Method 1 utilizing a solution of 10 mL of 0.032 M Cu(NO$_3$)$_2$ in 0.25M sodium acetate in the final 5 minutes of Method 1 to create c(RGDyK)-Lys(DOTA-Cu) (0.25 mg, after purification on the same column and same procedure as in Method 1. LC-MS=Calcd. for C$_{43}$H$_{64}$CuN$_{13}$O$_{15}$: 1065.39 (m/z). found: 1064.39 [M–H]–; 531 [(M–2H/2]$^-$.

Compound (14): CCK4-DOTA-La)—NH$_2$. To a solution of NHS-DOTA (Macrocyclics), (4.0 mg, 6.30×10$^{-3}$ mmol) dissolved in NMP (1.0 mL), the targeting peptide CCK4 amide (Bachem) (3.76 mg, 6.30×10$^{-3}$ mmol) in NMP (1.0 mL) with DIPA (8.14 mg, 6.30×10$^{-2}$ mmol) and TSTU (3.79 mg, 1.26×10$^{-2}$ mmol) was added. The solution was stirred for 4 hours at room temperature while using LC-MS method B: 5-100% to check the reaction progress. Once the reaction was complete, the solid La(NO$_3$)$_2$ (6.82 mg, 1.57×10$^{-2}$ mmol) was added, again following by LC-MS method B:

20-100% to check the reaction progress which was immediate. Diethyl ether (5 mL) was added to precipitate the product which was vortexed and centrifuged in a 15 mL centrifuge tube This product was purified through SPE using method B: 5-50% with product CCK4-DOTA-La)—$NH_2$ found in fractions 20-50%. Yield: 3.1 mg ($2.77 \times 10^{-3}$ mmol, 44.5%); LC-MS=Calcd. for $C_{45}H_{59}LaN_{10}O_{13}S$: 1118.30 (m/z). found: 1117.40 $[M-H]^-$; 558.2 $[(M-2H/2]^-$.

Compound (15): CCK-4-Lys(DOTA-Cu)—$NH_2$. A solution of CCK4-DOTA-La)—$NH_2$ (14) (0.5 mg) was transmetalated by the two-step Method 1 utilizing a solution of 20 mL of 0.032 M $Cu(NO_3)_2$ in 0.25 M sodium acetate in the final 5 minutes to create the product mg CCK-4-Lys(DOTA-Cu)—$NH_2$ after purification on the same column as transmetalation and same procedure LC-MS=Calcd. for $C_{45}H_{59}CuN_{10}O_{13}S$: 1042.33 (m/z). found: 1041.73 $[M-H]^-$; 520.5 $[(M-2H/2]^-$.

Compound (16): SMCC-Lys(DOTA-La)—$NH_2$. To a solution of (4) Fmoc-Lys(DOTA-La)—$NH_2$ (88.0 mg, 0.10 mmol) dissolved in DMF (8 mL), DEA (71.3 mg, 1.0 mmol) was added drop-wise. The solution was stirred for 2 hours at room temperature while using LC-MS method A: 20-100% to check the reaction progress every 0.5 hours. Once the reaction was complete, the material was rotary evaporated. This concentrated material was then dissolved in $H_2O$ and added to a separatory funnel for extraction using pure EtOAc for the organic layer and water for the aqueous layer. A sequential back extraction was done on the aqueous layers with a single layer of EtOAc. Product was found in the aqueous layer which was concentrated and dried in a vacuum. Yield of H-Lys(DOTA-La)—$NH_2$: 63.0 mg ($0.95 \times 10^{-2}$ mmol, 95.0%); LC-MS=Calcd. for $C_{22}H_{38}LaN_7O_8$: 667.18 (m/z). found: 666.3 $[M-H]^-$, 668.4 $[M+H]^+$, To a solution of H-Lys(DOTA-La)—$NH_2$ (55.00 mg, $8.16 \times 10^{-2}$ mmol) dissolved in PBS buffer (1 mL) of pH 8.5, the SMCC linker (17.51 mg, $5.24 \times 10^{-2}$ mmol) in DMF (2 mL) was added. The solution was stirred for 1.5 h at room temperature while using LC-MS method B: 20-100% to check the reaction progress every 0.5 h. Once the reaction was complete, the material was concentrated in a vacuum. The product was purified through SPE method B: 10-50%. The product was found in fractions 15-25%. Yield: 22.1 mg ($2.5 \times 10^{-2}$ mmol, 30.5%); LC-MS=Calcd. for $C_{34}H_{51}LaN_8O_{11}$: 886.27 (m/z). found: 885.5 $[M-H]^-$.

Compound (17): c(RGDyK)-SMCC-Lys(DOTA-La)—$NH_2$. To a solution of SMCC-Lys(DOTA-La)—$NH_2$ (14) (7.50 mg, $8.48 \times 10^{-3}$ mmol) dissolved in NMP (2.5 mL), the targeting peptide c(RGDyK) (5.25 mg, $8.48 \times 10^{-3}$ mmol) in NMP (2.5 mL) with NMM (4.23 mg, $4.23 \times 10^{-2}$ mmol) was added. The solution was stirred for 24 hours at room temperature while using LC-MS method B: 20-100% to check the reaction progress. After 24 hours, additional NMM (1.66 mg, $1.64 \times 10^{-3}$ mmol) was added to the reaction mixture. Once the reaction was complete, 5 mL of ether was added to the reaction, this was transferred to a centrifuge tube and vortexed then centrifuged, ether decanted and white powder dried. The product was purified through SPE method B: 10-50%. The product was found in fractions 10-20%. The product was freeze dried, Yield: 12.2 mg ($1.16 \times 10^{-3}$ mmol, 34.9.00/%); LC-MS=Calcd. for $C_{61}H_{93}LaN_{17}O_{19}$: 1506.58 (m/z). found: 1505.4 $[M-H]^-$, 752.2 $[(M-2H)/2]^-$.

Compound (18): c(RGDyK)-SMCC-Lys(DOTA-Cu)—$NH_2$. A solution c(RGDyK)-SMCC-Lys(DOTA-La)—$NH_2$ (15) (9.7 mg, $6.44 \times 10^{-3}$ mmol) was dissolved in 1.5 mL water, loaded onto an HPLC column and transmetalated by the two-step Method 1 including pumping 3.5 L of 0.1 M TFA containing 1% methanol for six hours at 10 mL per minute followed by neutralizing the column as in Method 1 and pumping a solution of 0.120 g $Cu(NO_3)_2$ in 0.25 M NaOAc in 20 mL water eluting the product in fraction tubes by pumping 50% acetonitrile-wate to yield the PET agent c(RGDyK)-SMCC-Lys(DOTA-Cu)—$NH_2$ after concentration and freeze drying. Yield: 7.5 mg ($1.16^{-3}$ mmol, 34.9.0%); LC-MS=Calcd. for $C_{61}H_{93}CuN_{17}O_{19}$: 1430.61 (m/z). found: 1429.2 $[M-H]^-$, 714.4 $[(M-2H)/2]^-$.

Compound (19): c(RGDyK)-SMCC-dK(DOTA-La)—K(DOTA-Gd)—$NH_2$: The precursor for this precursor for a PET-MRI agent was made in analogous manner to the procedure described for the analogous di-gadolinium compound prepared in U.S. Patent Application Publication No. US 2015/0038672. The precursor, SMCC-dK(DOTA-La)—K(DOTA-Gd)—$NH_2$ (8.0 mg, $5.14 \times 10^{-3}$ mmol was dissolved in 2.0 mL of NMP followed by the addition of c(RGDyK) (Peptides International) (3.19 mg, 5.14 mmol) and NMM (5.20 mg, $5.14 \times 10^{-2}$ mmol). This was stirred for 48 hours and monitored by LC-MS method B: 5-100% to check the reaction progress. The reaction was incomplete so it was heated at 40° C. for another 48 hours. When the reaction was complete, 5 mL of ether was added to the reaction, this was transferred to a centrifuge tube and vortexed then centrifuged, ether decanted and white powder dried. The product was purified through SPE method B: 10-50%. The product was found in fractions 5-20%. The product was freeze dried, Yield: 3.2 mg ($1.16^{-3}$ mmol, 34.9.0%); LC-MS=Calcd. for $Cs_3H_{127}GdLaN_{23}O_{27}$: 2174.76 (m/z). found, 1086.38 $[(M-2H)/2]^-$, 724.3 $[(M-3H)/3]^-$.

Compound (20): c(RGDyK)-SMCC-dK(DOTA-Cu)—K(DOTA-Gd)—$NH_2$: A solution c(RGDyK)-SMCC-dK(DOTA-Cu)—K(DOTA-Gd)—$NH_2$ (19) (1.0 mg, $4.83 \times 10^4$ mmol) was dissolved in 1.5 mL water, loaded onto an HPLC column and transmetalated by the two-step Method 1 including pumping 3.0 L of 0.1 M TFA containing 1% methanol for six hours at 10 mL per minute followed by neutralizing the column as in Method 1 and pumping a solution of 0.120 g $Cu(NO_3)_2$ in 0.25 M NaOAc in 20 mL water eluting the product in fraction tubes by pumping 50% acetonitrile-water to yield the PET agent c(RGDyK)-SMCC-dK(DOTA-Cu)—K(DOTA-Gd)—$NH_2$ after concentration and freeze drying. Yield: 0.4 mg ($1.90^{-4}$ mmol, 39.5%); LC-MS=Calcd. for $C_{61}H_{93}CuN_{17}O_{19}$: 1430.61 (m/z). found: 1429.2 $[M-H]^-$, 714.4 $[(M-2H)/2]^-$.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A process for the preparation of a radionuclide imaging agent, comprising:
providing an imaging agent comprising a chelated placeholder metal from Row 5 or 6 of the Periodic Table of Elements;
loading the imaging agent onto a stationary phase stable to an acidic solution comprising a dilute aqueous solution of strong acid, pKa<about 2, in a concentration of about 1.0 M or less or a solution of a weak organic acid, pKa>about 2 and <about 5, in a concentration of about 5.0 M or less;
binding the loaded imaging agent onto the stationary phase;

reacting the chelated place-holder metal by flowing an acidic solution comprising a dilute aqueous solution of strong acid, pKa<about 2, in a concentration of about 1.0 M or less or a solution of a weak organic acid, pKa>about 2 and <about 5, in a concentration of about 5.0 M or less through the stationary phase sufficient to remove the place-holder metal from the stationary phase bound imaging agent;

binding a replacement radioactive metal to the stationary phase bound imaging agent so as to replace the chelated place-holder metal of the imaging agent loaded on the stationary phase with the replacement radioactive metal; and eluting the imaging agent comprising the chelated replacement radioactive metal from the stationary phase to provide a radionuclide imaging agent suitable for positron emission tomography or single-photon emission computed tomography.

2. The process of claim 1, wherein replacing the place-holder metal with the replacement radioactive metal comprises a period of time of less than about 24 hours.

3. The process of claim 1, wherein binding a replacement radioactive metal to the stationary phase bound imaging agent comprises flowing a solution comprising a radioactive metal through the loaded stationary phase to replace the removed place-holder metal with the radioactive metal.

4. The process of claim 1, wherein the flowing an acidic solution through the loaded stationary phase comprises a period of time of less than about 24 hours.

5. The process of claim 3, wherein the flowing a solution comprising a radioactive metal through the loaded stationary phase comprises a period of time of less than about 8 hours.

6. The process of claim 1, wherein reacting the chelated place-holder metal and binding the replacement radioactive metal to the stationary phase bound imaging agent comprises flowing a solution comprising an acid and a radioactive metal over the loaded stationary phase to remove and replace the chelated place-holder metal of the imaging agent with the radioactive metal.

7. The process of claim 6, wherein removing and replacing the chelated place-holder metal of the imaging agent with the radioactive metal comprises a period of time of less than about 8 hours.

8. The process of claim 3, wherein the solution comprising a radioactive metal comprises a solution having a molarity of about 0.01 M to about 5.0 M of the radioactive metal.

9. The process of claim 1, wherein the stationary phase comprises a chromatography column or a reverse phase C18 column.

10. The process of claim 1, wherein the imaging agent is DOTA, DTPA, NOTA, TETA, TACN, CB-TE2A, Cyclen, DO2A, DO3A, DOT, DOTAM, or CB-Cyclam.

11. The process of claim 1, wherein the replacement radioactive metal is $^{64}$Cu, $^{68}$Ga, $^{86}$Y, $^{89}$Zr, $^{99}$Tc, or $^{111}$In.

12. The process of claim 1, wherein the imaging agent comprises a targeted imaging agent.

13. The process of claim 12, wherein the replacing comprises flowing an acidic solution over the loaded stationary phase and flowing a radioactive metal solution over the loaded stationary phase and wherein the acidic solution comprises reaction conditions sufficient to maintain the targeting capacity of the targeted imaging agent, wherein the targeted radionuclide imaging agent is suitable for use in a PET or SPECT molecular imaging technique.

* * * * *